US007034008B2

(12) United States Patent
Donahue et al.

(10) Patent No.: US 7,034,008 B2
(45) Date of Patent: Apr. 25, 2006

(54) CARDIAC ARRHYTHMIA TREATMENT METHODS

(75) Inventors: J. Kevin Donahue, Towson, MD (US); Eduardo Marban, Lutherville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/947,953

(22) Filed: Sep. 6, 2001

(65) Prior Publication Data

US 2002/0155101 A1 Oct. 24, 2002

Related U.S. Application Data

(60) Provisional application No. 60/295,889, filed on Jun. 5, 2001, provisional application No. 60/230,311, filed on Sep. 6, 2000.

(51) Int. Cl.
*A61K 31/711* (2006.01)
*A61M 25/095* (2006.01)

(52) U.S. Cl. ........................................ 514/44; 604/528

(58) Field of Classification Search ................ 604/187, 604/21; 514/44; 424/93.2; 435/320.1, 455, 435/91.4
See application file for complete search history.

(56) References Cited

U.S. PATENT DOCUMENTS

| | | | | |
|---|---|---|---|---|
| 5,163,950 | A * | 11/1992 | Pinchuk | 606/192 |
| 5,436,128 | A | 7/1995 | Harpold et al. | |
| 5,662,585 | A * | 9/1997 | Willis | 600/104 |
| 5,836,905 | A * | 11/1998 | Lemelson | 604/21 |
| 5,944,710 | A | 8/1999 | Dev et al. | |
| 6,086,582 | A | 7/2000 | Altman et al. | |
| 6,214,620 | B1 | 4/2001 | Johns et al. | |
| 6,309,375 | B1 * | 10/2001 | Glines | 604/187 |
| 2003/0195470 | A1 * | 10/2003 | Ponzi | 604/164.07 |

FOREIGN PATENT DOCUMENTS

| | | |
|---|---|---|
| WO | WO 96/28537 | 9/1996 |
| WO | WO 99/23880 | 5/1999 |
| WO | WO 00/18903 | 4/2000 |
| WO | WO 00/38518 | 7/2000 |
| WO | WO 00/41731 | 7/2000 |
| WO | WO 02/33111 | 4/2002 |

OTHER PUBLICATIONS

Chen et al., Am J Physiol Heart Circ Physiol, vol. 280, H1989-H1995, 2001.*
Bauer et al., Circulation, 110:3115-3120, 2004.*
Schroder, Expert Opin. Biol. Ther., vol. 4, 9:1413-1422, 2004.*

Donahue, J.K., et al., "Ultrarapid, Highly Efficient Viral Gene Transfer to the Heart", Proc. Natl. Acad. Sci. USA, vol. 94, pp. 4664-4668, (Apr. 1997).
Donahue, J.K., et al., "Acceleration of Widespread Adenoviral Gene Transfer to Intact Rabbit Hearts by Coronary Perfusion With Low Calcium and Serotonin", Gene Therapy, vol. 5, pp. 630-634, (1998).
Muhlhauser, J., et al., "Safety and Efficacy of In Vivo Gene Transfer Into the Porcine Heart with Replication-Deficient, Recombinant Adenovirus Vectors", Gene Therapy, vol. 3, pp. 145-153, (1996).
French, B.A., et al., "Direct in Vivo Gene Transfer Into Porcine Myocardium Using Replication-Deficient Adenoviral Vectors", Circulation, vol. 90, No. 5, pp. 2414-2424 (Nov. 1994).
Akhter, S.A., et al., "Restoration of β-adrenergic Signaling in Failing Cardiac Ventricular Myocytes via Adenoviral-mediated Gene Transfer", Proc. Natl. Acad. Sci. USA, vol. 94, pp. 12100-12105, (Oct. 1997).
Donahue, J.K., et al., "Focal Modification of Electrical Conduction in the Heart by Viral Gene Transfer", Nature Medicine, vol. 6, No. 12, pp. 1395-1398, (Dec. 2000).
Tomaselli, G.F., et al., "Electrophysiological Remodeling in Hypertrophy and Heart Failure", Cardiovascular Research, vol. 42, pp. 270-283, (1999).
Marban, E., "Circulation Research Impact Factor Sets New Record", Circulation Research, vol. 89, p. 101, (2001).
Lalli, M.J., et al., "Sarcoplasmic Reticulum $Ca^{2+}$ ATPase (SERCA) 1a Structurally Substitutes for SERCA2a in the Cardiac Sacroplasmic Reticulum and Increases Cardiac $Ca^{2+}$ Handling Capacity", vol. 89, pp. 160-167, (2001).
Mazhari, R., et al., "Molecular Interactions Between Two Long-QT Syndrome Gene Products, HERG and KCNE2, Rationalized by *In Vitro* and *In Silico* Analysis", Circ. Res., vol. 89, pp. 33-38, (2001).
Sugiyama, A., et al., "Measurement of Adenylylcyclase Activity in the AV Nodal Region of the Canine Heart: Evidence for Inhibition by Adenosine and Acetylcholine", Journal of Cardiovascular Pharmacology, vol. 29, pp. 734-739, (1997).
Yamagishi, T., et al., "Molecular Architecture of the Voltage-dependent Na Channel: Functional Evidence for a Helices in the Pore", J. Gen. Physiol., vol. 118, pp. 171-181, (2001).
Seharaseyon, J., et al., "Molecular Composition of Mitochondrial ATP-Sensitive Potassium Channels Probed by Viral Kir Gene Transfer", J. Mol. Cell Cardiol., vol. 32., pp. 1923-1930, (2000).

(Continued)

*Primary Examiner*—James Ketter
*Assistant Examiner*—Patrick S. Riggins
(74) *Attorney, Agent, or Firm*—Banner & Witcoff, Ltd.

(57) ABSTRACT

Disclosed are methods of preventing or treating cardiac arrhythmia. In one embodiment, the methods include administering to an amount of at least one polynucleotide that modulates an electrical property of the heart. The methods have a wide variety of important uses including treating cardiac arrhythmia.

15 Claims, 10 Drawing Sheets

OTHER PUBLICATIONS

Kass-Eisler, A., et al., "Quantitative Determination of Adenovirus-Mediated Gene Delivery to Rat Cardiac Myocytes *In Vitro* and *In Vivo*", Proc. Natl. Acad. Sci. USA., vol. 90, pp. 11498-11502, (Dec. 1993).

Johns et al. "Adenovirus-Mediated Expression of a Voltage-Gated Potassium Channel *in vitro* (Rat Cardiac Myocytes) and *in vivo* (Rat Liver). A Novel Strategy For Modifying Excitability", J. Clin. Invest. Aug. 1995, vol. 96, pp. 1152-1158.

Hoppe et al. "Adenovirus-Mediated Inducible Gene Expression *In Vivo* By a Hybrid Ecdysone Receptor", Molecular Therapy, Feb. 2000, vol. 1, No. 2, pp. 159-164.

Hoppe et al. "Molecular Dissection of Cardiac Repolarization By *In Vivo* Kv4.3 Gene Transfer", Journal of Clinical Investigation, Apr. 2000, vol. 105, No. 8, pp. 1077-1084.

A copy of International Search Report dated Jun. 5, 2002 re corresponding International Application No. PCT/US01/27623, 4 pages.

Chiang C-E et al., The Long QT Syndromes: Genetic Basis and Clinical Implications, *J. Amer. Coll. Cardiology*, vol. 36, No. 1, Jul. 2000, pp. 1-12.

Gros DB et al., "Connexins in mammalian heart function," *Bioessays*, vol. 18, No. 9, 1996, pp. 719-730.

Hajjar RJ et al., "Prospects for gene therapy for heart failure," *Circulation Research*, vol. 86, No. 6, Mar. 31, 2000, pp. 616-621.

Hoppe Uta C et al., "Distinct gene-specific mechanisms of arrhythmia revealed by cardiac gene transfer of two long QT disease genes," *HERG and KCNE1 Proceedings of the National Academy of Sciences of the United States of America*, vol. 98, No. 9, Apr. 24, 2001, pp. 5335-5340.

Johns, DC et al., "Suppression of neuronal and cardiac transient outward currents by viral gene transfer of dominant-negative Kv4.2 constructs," *J. Bio. Chem.* vol. 272, No. 50 (Dec. 12, 1997), pp. 31598-31603.

Lawrence JH et al., "Prospects for genetic manipulation of cardiac excitability," *Advances in Experimental Medicine and biology*, vol. 382, 1995, pp. 41-48.

Marban E. et al., "Gene Therapy for Cardiac Arrhythmias," *Cold Spring Harbor Symposia on Quantitative Biology*, vol. 67, 2002, pp. 527-531.

Nuss HB et al., "Overexpression of a human potassium channel suppresses cardiac hyperexcitability in rabbit ventricular myocytes," *J. Clin. Invest.* vol. 103, No. 6, Mar. 1999, pp. 889-896.

Nuss HB et al., "Reversal of Potassium Channel deficiency in Cells from Failing Hearts by Adenoviral Gene Transfer: A Prototype for Gene Therapy for Disorders of Cardiac Excitability and Contractility," *Gene Therapy*, vol. 3, No. 3, Oct. 1996, pp. 900-912.

\* cited by examiner

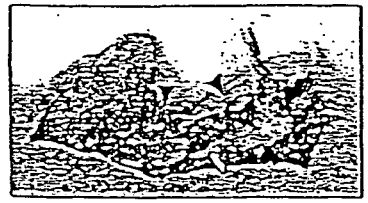
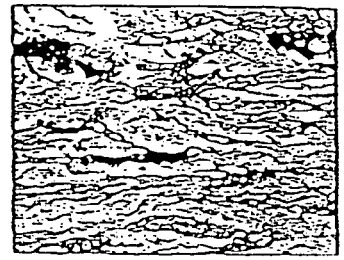
FIG. 1A          FIG. 1B
KIDNEY          KIDNEY
      
OVARY   LUNG      OVARY   LUNG
      
SKELETAL MUSCLE   LIVER      SKELETAL MUSCLE   LIVER
FIG. 1C          FIG. 1D

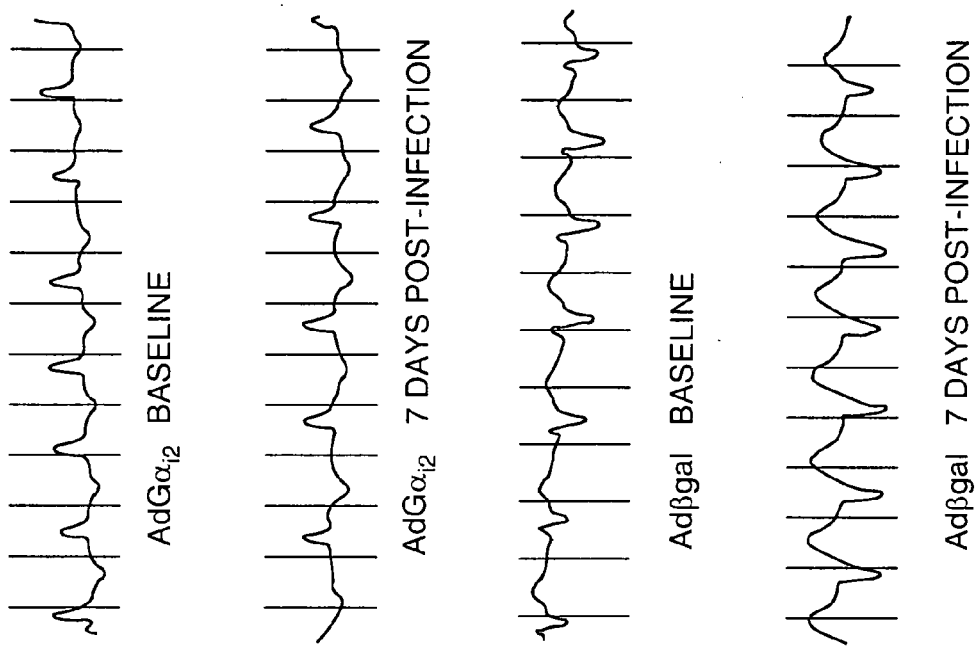
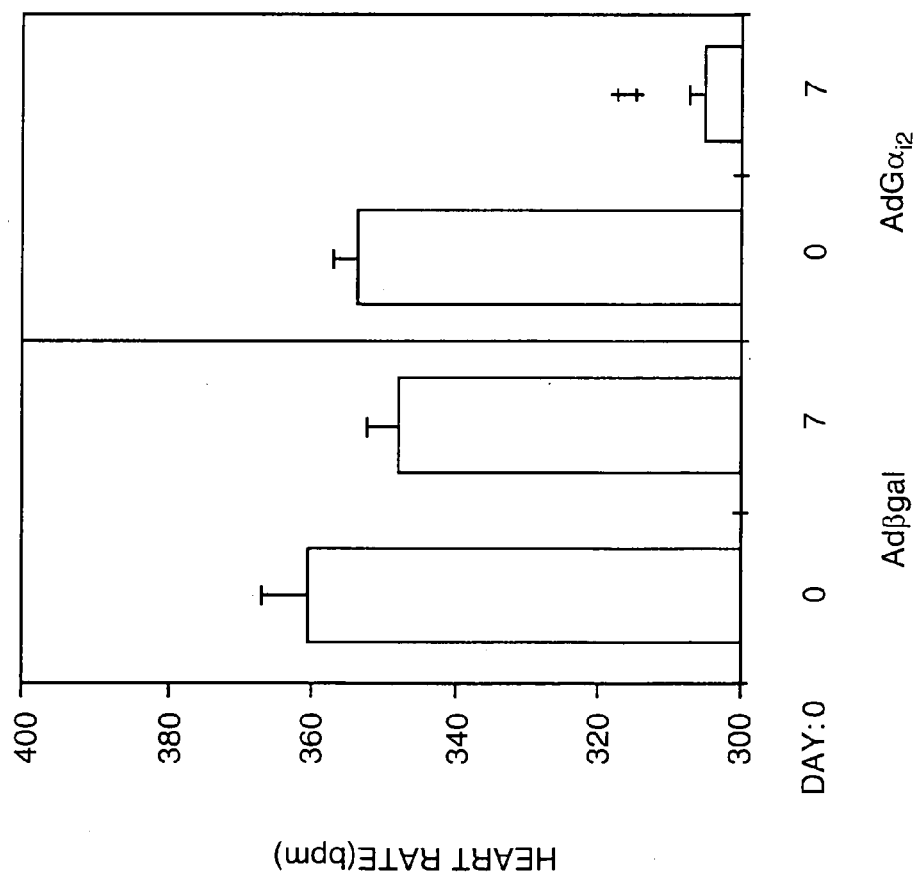
FIG. 3B
FIG. 3A

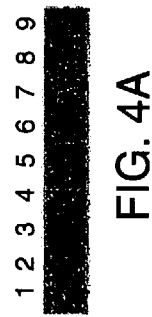
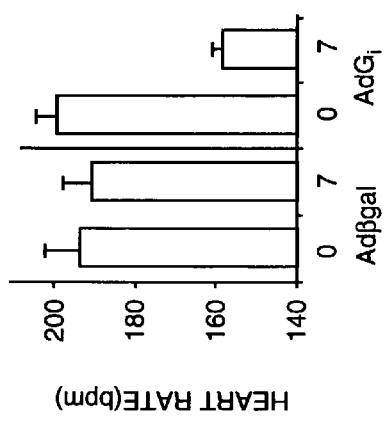
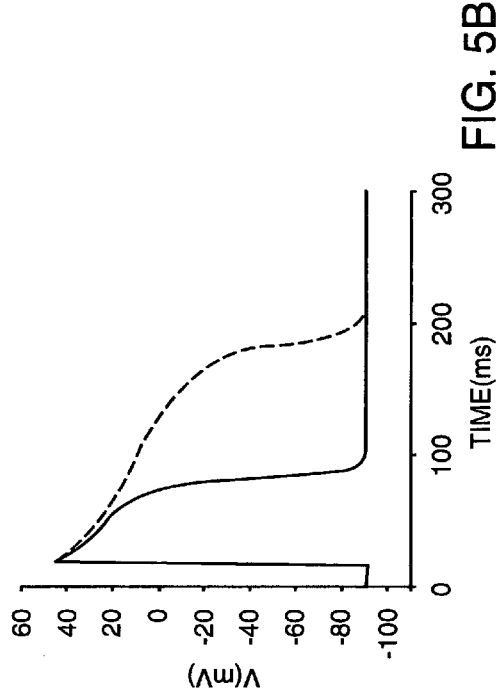
FIG. 4A
FIG. 4B
FIG. 5A
FIG. 5B

Amino acid sequence of human Gα$_{i2}$ (NCBI protein sequence #P04899)

```
  1 mgctvsaedk aaaerskmid knlredgeka arevkllllg agesgkstiv kqmkiihedg
 61 yseeecrqyr avvysntiqs imaivkamgn lqidfadpsr addarqlfal sctaeeqgvl
121 pddlsgvirr lwadhgvqac fgrsreyqln dsaayylndl eriaqsdyip tqqdvlrtrv
181 kttgivethf tfkdlhfkmf dvggqrserk kwihcfegvt aiifcvalsa ydlvlaedee
241 mnrmhesmkl fdsicnnkwf tdtsiilfln kkdlfeekit hsplticfpe ytgankydea
301 asyiqskfed lnkrkdtkei ythftcatdt knvqfvfdav tdviiknnlk dcglf
```

FIG. 9A

Nucleotide sequence of human Gα$_{i2}$

Exon 1:

```
  1 cccggccttt ttttttccft tttcgactag ctgcaaccca gagggagaag gcggtaaacc
 61 cgccttaaga ctgagaaaac cgcagtccag aaaggctccc gagttcgtag atcccaaaac
121 aagtttactg gactcattaa ctttaacaaa tgacaaagac acgcctcctc cacctaactc
181 gcccaactcg cagaagctca gagggctggt tcctgctctg ccctcgaggg caccgatccc
241 caccctcggg ttaacagatc cgccctcccg gctgtccagc aacagagctc ccggcgctcc
301 gcacccaatc acagcccggt ccgcctgca gcccgcccag tgccgggtcc cggggtttgg
361 aaccacccct attgccttt ctccgcgtgg ccccgcctgc acccaggccc gagcctgggc
421 tgcctaactt cccccttcgc tccgccctcg agccaatcaa cagcctctaa tctcctctgg
481 cccgcctgc aagcccgccc cggcccagtc acaggcttgg ttcgcccagg ccccaccccc
541 ggcccgcccc gccgtcggtg cgcggcggta gggaaggcgc ctcccgcagt cgctcggaac
601 tgccgacccg agtgcttccc gcagagggct ggtggtggga gcggagtggg tcgggcgggg
661 ccgagccggg ccgtgggccg tgtgggggcc gggcggcggc cgggccggcg gacggcggga
721 tgggctgcac cgtgagcgcc gaggacaagg cggcggccga gcgctctaag atgatcgaca
781 agaacctgcg ggaggacgga gagaaggcgg cgcgggaggt gaagttgctg ctgttgggtg
841 agg
```

Exon 2:

```
  1 gccctctgtt ccaggtgctg gggagtcagg gaagagcacc atcgtcaagc agatgaagta
 61 agt
```

Exon 3:

```
  1 gtcctggcta tcaggatcat ccacgaggat ggctactccg aggaggaatg ccggcagtac
 61 cgggcggttg tctacagcaa caccatccag tccatcatgg ccattgtcaa agccatgggc
121 aacctgcaga tcgactttgc cgacccctcc agagcggtat gt
```

Exon 4:

```
  1 gccactgtgc ccaggacgac gccaggcagc tatttgcact gtcctgcacc gccgaggagc
 61 aaggcgtgct ccctgatgac ctgtccggcg tcatccggag gctctgggct gaccatggtg
121 tgcaggcctg ctttggccgc tcaagggaat accagctcaa cgactcagct gcctagtgag
181 t
```

Exon 5:

```
  1 cccccatcc ccagctacct gaacgacctg gagcgtattg cacagagtga ctacatcccc
 61 acacagcaag atgtgctacg gacccgcgta aagaccacgg ggatcgtgga gacacactc
121 accttcaagg acctacactt caagtgagc
```

FIG. 9B

Exon 6:

```
  1 ctgcaggatg tttgatgtgg gtggtcagcg gtctgagcgg aagaagtgga tccactgctt
 61 tgagggcgtc acagccatca tcttctgcgt agccttgagc gcctatgact tggtgctagc
121 tgaggacgag gagatggtga ga
```

Exon 7:

```
  1 tattctaccc ccagaaccgc atgcatgaga gcatgaagct attcgatagc atctgcaaca
 61 acaagtggtt cacagacacg tccatcatcc tcttcctcaa caagaaggac ctgtttgagg
121 agaagatcac acacagtccc ctgaccatct gcttccctga gtacacaggt gtgg
```

Exon 8:

```
  1 tttctctccc ccaggggcca acaaatatga tgaggcagcc agctacatcc agagtaagtt
 61 tgaggacctg aataagcgca aagacaccaa ggagatctac acgcacttca cgtgcgccac
121 cgacaccaag aacgtgcagt tcgtgtttga cgccgtcacc gatgtcatca tcaagaacaa
181 cctgaaggac tgcggcctct ctgaggggc agcggggcct ggcgggatgg tgatc
```

Exon 9:

```
  1 gctttccccc acctccaggg ccaccgccga ctttgtaccc cccaacccct gaggaagatg
 61 ggggcaagaa gatcacgctc cccgcctgtt ccccgccgc ttttctcctc tttcctctct
121 ttgttctcag ctcccctgt cccctcagct ccagacgtag gggagggtt gccacaggcc
181 tccctgtttg aagcctgccc ttgtctgaga tgctggtaat ggccatggta cccccttctg
241 ggcatctgtt ctggttttta accattgtct tgttctgtga tgaggggagg ggggcacatg
301 ctgagtctcc caaggctgcg tctggagggg cccctgcttc tccagcctgg accccagct
361 ttgcccaaca ccagcccctg ccccagccca agtccaaatg tttacaggga gcctcctgcc
421 cagtccccca accccagccg ctcggaggcc ccaaaggaaa aagcacaaga agcgtgagac
481 gccaccattc ctggaaacca cagtccacct gctcattctc gtagcttttt aaaaaaatga
541 aagtaaagga aaaaaaaaa actgaaatct agaaaacttt ttagagaaaa actatttaaa
601 actgtcagat cctgaccagc aagcccccc ccagccccc ttccaagtga ctccgtgcct
661 tgagtgtgtc tgcgtgttta cacccgtccc tctgctggcc gcccccgtgc gagcggcacc
721 cctgccctgc cctccacaga attgggttcc aagggctgtt ccagacaact gccaacgtca
781 ctgagggccc tgccccagcg gccctggccc caggctctat taacctaaaa tgtagctccc
841 tagcgctaac ctaggaaccg ccgctgcctg ctggggggcc acgcccctca tgcccttgtc
901 ccaggcccgg ggccttcagc gttgaacact tccttgcttt tttcacatgt tttatggaat
961 tgttcacctg gtttgaaata ataaaatgta gaaagaaaaa aaataccgag aactgatggg
1021 tattctctcc cagggg
```

FIG. 9C

CARDIAC ARRHYTHMIA TREATMENT METHODS

CROSS-REFERENCE TO RELATED APPLICATION

The present application claims priority to United States Provisional Application No. 60/230,311, filed on Sep. 6, 2000, and United States Provisional Application No. 60/295,889, filed on Jun. 5, 2001, the disclosure of which are both incorporated herein by reference.

STATEMENT OF FEDERALLY SPONSORED RESEARCH

Funding for the present invention was provided in part by the Government of the United States by virtue of Grant No. NIH P50 HL52307 by the National Institutes of Health. Thus, the Government of the United States has certain rights in and to the invention claimed herein.

FIELD OF THE INVENTION

The invention generally features methods for the prevention or treatment of heart arrhythmia. Preferred methods generally involve administering at least one therapeutic polynucleotide to a mammal sufficient to modulate at least one electrical property of the heart. Modulation of the electrical property addresses the arrhythmia typically by encouraging normal heart electrical function.

BACKGROUND

The mammalian heart is understood to maintain an intrinsic rhythm by creating electric stimuli. Generally, the stimuli form a depolarization wave that propagates within specialized cardiac conducting tissue and the myocardium. The usually well-ordered wave movement facilitates coordinated contractions of the myocardium. These contractions are the engine that moves blood throughout the body. See generally *The Heart and Cardiovascular System. Scientific Foundations*. (1986) (Fozzard, H. A. et al. eds) Raven Press, NY.

Under most circumstances, cardiac stimuli are controlled by recognized physiological mechanisms. However there has been long-standing recognition that abnormalities of excitable cardiac tissue can lead to abnormalities of the heart rhythm. These abnormalities are generally referred to as arrhythmias. Most arrhythmias are believed to stem from defects in cardiac impulse generation or propagation that can substantially compromise homeostasis, leading to substantial patient discomfort or even death. For example, cardiac arrhythmias that cause the heart to beat too slowly are known as bradycardia, or bradyarrhythmia. In contrast, arrhythmias that cause the heart to beat too fast are referred to as tachycardia, or tachyarrhythmia. See generally *Cardiovascular Arrhythmias* (1973) (Dreifus, L. S. and Likoff, W. eds) Grune & Stratton, NY.

The significance of these and related heart disorders to public health cannot be exaggerated. Symptoms related to arrhythmias range from nuisance, extra heart beats, to life-threatening loss of consciousness. Complete circulatory collapse has also been reported. Morbidity and mortality from such problems continues to be substantial. In the United States alone for example, cardiac arrest accounts for 220,000 deaths per year. There is thought to be more than 10% of total American deaths. Atrial fibrillation, a specific form of cardiac arrhythmia, impacts more than 2 million people in the United States. Other arrhythmias account for thousands of emergency room visits and hospital admissions each year. See eg., Bosch, R. et al. (1999) in *Cardiovas Res.* 44: 121 and references cited therein.

Cardiac electrophysiology has been the subject of intense interest. Generally, the cellular basis for all cardiac electrical activity is the action potential (AP). The AP is conventionally divided into five phases in which each phase is defined by the cellular membrane potential and the activity of potassium, chloride, and calcium ion channel proteins that affect that potential. Propagation of the AP throughout the heart is thought to involve gap junctions. See Tomaselli, G. and Marban, E. (1999) in *Cardiovasc. Res.* 42: 270 and references cited therein.

There have been limited attempts to treat cardiac arrhythmias and related heart disorders.

Specifically, many of the past attempts have been confined to pharmacotherapy, radiofrequency ablation, use of implantable devices, and related approaches. Unfortunately, this has limited options for successful patient management and rehabilitation.

In particular, radiofrequency ablation has been reported to address a limited number of arrhythmias eg., atrioventricular (AV) node reentry tachycardia, accessory pathway-mediated tachycardia, and atrial flutter. However, more problematic arrhythmias such as atrial fibrillation and infarct-related ventricular tachycardia, are less amenable to this and related therapies. Device-based therapies (pacemakers and defibrillators, for instance) have been reported to be helpful for some patients with bradyarrhythmias and lifesaving for patients with tachyarrhythmias. However, such therapies does not always prevent tachyarrhythmias. Moreover, use of such implementations is most often associated with a prolonged commitment to repeated procedures, significant expense, and potentially catastrophic complications including infection, cardiac perforation, and lead failure.

Drug therapy remains a popular route for reducing some arrhythmic events. However, there has been recognition that systemic effects are often poorly tolerated. Moreover, there is belief that proarrhythmic tendencies exhibited by many drugs may increase mortality in many situations. See generally Bigger, J. T and Hoffman, B. F. (1993) in *The Pharmacological Basis of Therapuetics* $8^{th}$ Ed. (Gilman, A. G et al. eds) McGraw-Hill, NY and references cited therein.

It would be desirable to have more effective methods for treating or preventing cardiac arrhythmias. It would be especially desirable to have gene therapy methods for treating or preventing such arrhythmias.

SUMMARY OF THE INVENTION

The present invention provides methods of preventing or treating cardiac arrhythmia in a mammal. In general, the methods involve administering to the mammal at least one polynucleotide that preferably modulates at least one electrical property of the heart. Use of the polynucleotides according to the invention modulates the heart electrical property, thereby preventing or treating the cardiac arrhythmia.

There has been a long-felt need for more effective anti-arrhythmic therapies. The invention addresses this need by providing, for the first time, therapeutic methods for administering one or more therapeutic polynucleotides to the heart under conditions sufficient to modulate (increase or decrease) at least one heart electrical property. Preferred use of the invention modulates heart electrical conduction preferably reconfigures all or part of the cardiac action potential (AP). That use helps achieve a desired therapeutic outcome. Significant disruption of normal electrical function is usually reduced and often avoided by the present methods. Moreover, use of the invention is flexible and provides, also for the first time, important anti-arrhythmic strategies that can be tailored to the health requirements of one patient or several as needed.

The invention provides other advantages that have been heretobefore difficult or impossible to achieve. For example, and unlike prior practice, the invention methods are genetically and spatially controllable ie., they provide for administration of at least one pre-defined polynucleotide to an identified heart tissue or focal area. Since there is recognition that many protein encoding polynucleotides can be expressed successfully in heart tissue, the invention is a generally applicable anti-arrhythmia therapy that can be employed to supply the heart with one or a combination of different therapeutic proteins encoded by the polynucleotides. Such proteins can be provided transiently or more long-term as needed to address a particular cardiac indication.

The invention provides further benefits and advantages. For example, practice of prior anti-arrhythmic approaches involving pharmacotherapy, radiofrequency ablation, and implantable device approaches is reduced and oftentimes eliminated by the invention. Moreover, the invention provides, highly localized gene delivery. Importantly, treated cells and tissue usually remain responsive to endogenous nerves and hormones in most cases. In particular invention methods discussed below, localized coronary circulation provides targeted delivery to isolated regions of the heart. In some embodiments, proximity to endocardium allows access by intracardiac injection. Therapeutic effects are often readily detected eg., by use of standard electrophysiological assays as provided herein. Also importantly, many gene transfer-induced changes in accord with the present invention can be rescued, if needed, by conventional electrophysiological methods.

Accordingly, and in one aspect, the invention provides methods for preventing or treating cardiac arrhythmia. More specific methods include administering to a mammal a therapeutically effective amount of at least one polynucleotide that can increase or decrease at least one electrical property as determined by one or more standard electrophysiological assays. Examples of preferred administration routes, polynucleotides, and assays are provided in the discussion that follows. Preferably, the invention further includes expressing the polynucleotide in the mammal sufficient to prevent or treat the cardiac arrhythmia. In general, polynucleotide expression conducive to using the invention is apparent as a shift in a recording (relative to baseline) obtained from at least one of the standard electrophysiological assays.

In additionally preferred invention methods, the electrical property is increased or decreased by at least about 10% relative to a baseline function. More preferably, the increase or decrease is at least about 20%, more preferably at least about 30% to about 50% or more. That baseline function can be readily ascertained eg., by performing the electrophysiological assay on a particular mammal prior to conducting the invention methods. Alternatively, related baseline function can be determined by performing a parallel experiment in which a control polynucleotide is administered instead of the polynucleotide of interest. It will be apparent that once a reliable baseline function has been established (or is available from public sources) determination of the baseline function by the practitioner may not always be necessary.

Examples of relevant electrical properties are known and include, but are not limited to, at least one of refractoriness, speed of conduction, focal automaticity, and spatial excitation pattern.

The invention is widely applicable to the prevent and treatment of a wide range of ventricular or atrial arrhythmias including atrial fibrillation. Accordingly, the invention provides, in one embodiment, methods for treating atrial fibrillation that include administering to a mammal a therapeutically effective amount of at least one polynucleotide encoding an inhibitory G protein subunit, preferably $G\alpha_{i2}$ subunit; or a functional fragment thereof. Preferred method practice involves expressing the polynucleotide in the mammal to treat the atrial fibrillation, particularly by controlling heart rate. Additional prevention and treatment methods are provided below.

In another aspect, the invention provides a kit for performing one or a combination of the invention methods disclosed herein. Preferably, the kit includes at least one suitable myocardium nucleic acid delivery system and preferably at least one desired polynucleotide. Preferably, that polynucleotide is operably linked to the system i.e., it is in functional and/or physical association therewith sufficient to provide for good administration of the polynucleotide into the heart. Additionally preferred kits include means for administering the polynucleotide to the mammal such as a syringe, catheter and the like.

The invention also includes a device useful for the therapeutic methods disclosed herein. Preferred devices include those unitary, integral devices elate position of the device within a subject, particularly proximate to a patient's heart, as well as deliver a therapeutic agent to a patient, particularly a nucleic acid therapeutic to a mammalian heart. Specifically preferred devices comprise an elongate member, particularly a flexible catheter member that can be advanced to a patient's heart. The catheter unit suitably comprises a administration member, e.g. a needle member, for delivering a therapeutic agent especially a polynucleotide to cardiac tissue of the patient. The catheter unit also includes positioning detection apparatus such as detetable electrodes at the catheter's distal end.

Other invention embodiments are disclosed below.

BRIEF DESCRIPTION OF THE DRAWINGS

FIGS. 1A–B are photographs showing gene transfer to the AV node after exposure to Adβgal. FIGS. 1C–D are photographs showing gene transfer to various non-target organ tissue.

FIG. 3A is a graph showing reduction in heart rate during atrial fibrillation after gene transfer of inhibitory G subunit ($G_{i2}$) and infusion of epinephrine. FIG. 3B is a related electrocardiogram.

FIG. 4A is a Western blot of AV nodal tissue showing $G_{i2}$ over expression. FIG. 4B is a graph showing heart rate following gene transfer.

FIG. 5A is a graph showing comparison of $I_{kr}$ current in presence and absence of gene transfer-mediated overexpression of HERG. FIG. 5B is a photograph showing related action potential (AP).

FIG. 8B shows the indicated area of device in expanded cross-section.

FIG. 9A is a drawing showing the amino acid sequence of the human $G\alpha_{i2}$ sequence (SEQ ID NO: ID NO: 10) (NCBI protein sequence no. P04899).

FIGS. 9B–C are drawings showing the nucleic acid sequence encoding the human $G\alpha_{i2}$ sequence shown in FIG. 9A. FIGS. 9B–C show the nucleic acid sequences (SEQ ID NO's: 1–9, respectively in order of appearance) in exon form.

DETAILED DESCRIPTION OF THE INVENTION

Figure 2B:
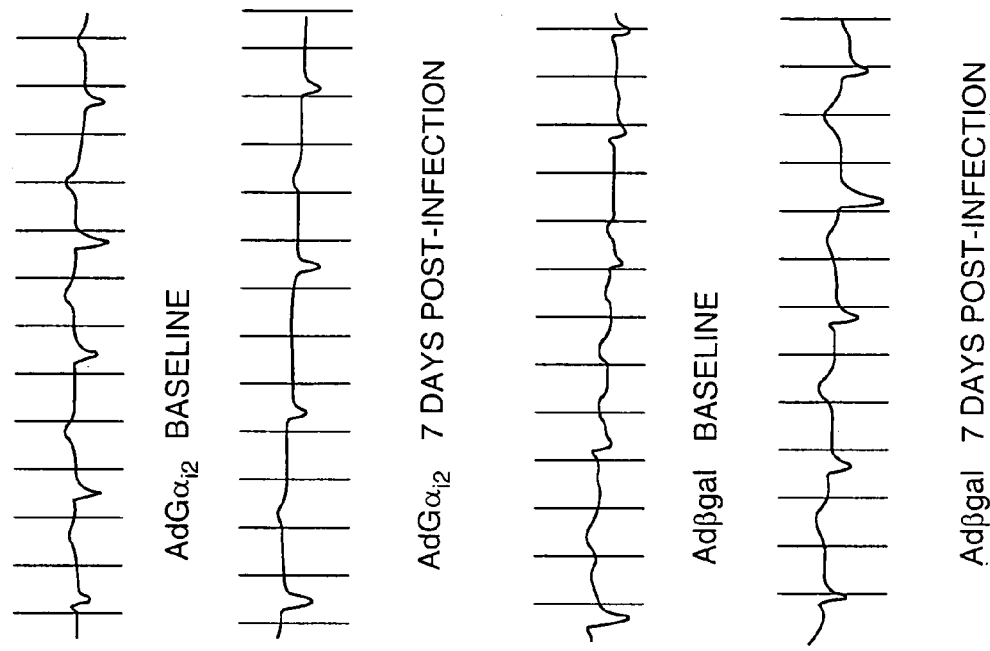
FIG. 2B is a related electrocardiogram.
Figure 2A:
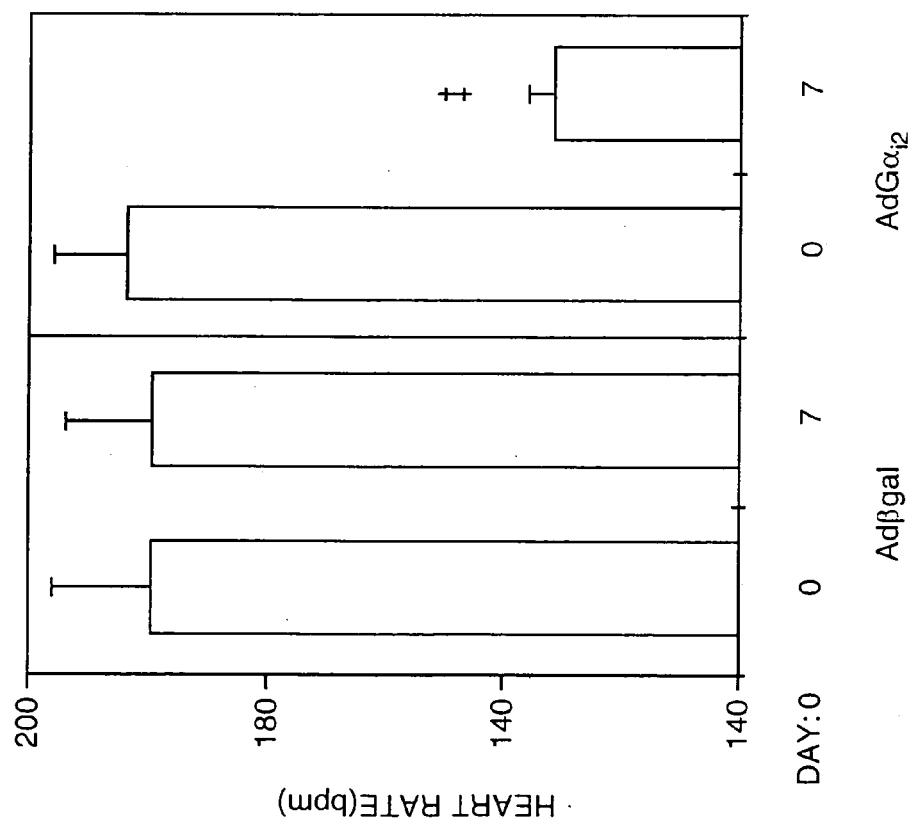
FIG. 2A is a graph showing reduction in heart rate during atrial fibrillation after gene transfer of inhibitory G subunit ($G_{i2}$)

As discussed, the invention provides methods for the prevention or treatment of cardiac arrhythmia in a subject mammal. By "treatment" is meant use of the invention to reduce the severity of, prolong onset, or eliminate one or a combination of cardiac arrhythmias. Preferred methods involve administering a therapeutically effective amount of at least one polynucleotide capable of modulating at least one heart electrical property. More preferred methods involve expression of the polynucleotide sufficient to prevent or treat the cardiac arrhythmia in the mammal.

Preferred mammals include domesticated animals eg., pigs, horses, dogs, cats, sheep, goats and the like; rodents such as rats, hamsters and mice; rabbits; and primates such as monkeys, chimpanzees ect. A highly preferred mammal is a human patient, preferably a patient who has or is suspected of having a cardiac arrhythmia. Methods of diagnosing and treating a variety of cardiac arrhythmias have been disclosed. See *Cardiovascular Arrhythmias* (1973) (Dreifus, L. S. and Likoff, W. eds) Grune & Stratton, NY; and references cited therein.

The invention is generally compatible with one or a combination of suitable polynucleotide administration routes including those intended for in vivo or ex vivo cardiac use. As discussed, there is understanding in the field that cardiac tissue is especially amenable to gene transfer techniques. See e.g, Donahue, J. et al. (1998) *Gene Therapy* 5: 630; Donahue, J. et al. *PNAS* (USA) 94: 4664 (disclosing rapid and efficient gene transfer to the heart); Akhter, S. et al. (1997) *PNAS* (USA) 94: 12100 (showing successful gene transfer to cardiac ventricular myocytes); and references cited therein.

See also the Examples and Drawings provided herein which demonstrate, inter alia, successful use of myocardial gene transfer techniques particularly to address cardiac arrhythmia.

Typically preferred invention methods feature administration routes in which expression of the introduced polynucleotide directly or indirectly causes a decrease in speed of conduction through at least one of: 1) the atrioventricular (AV) node (A-H interval) and 2) the His-Purkinje system. The decrease is readily detected and measured according to conventional means eg., by use of one or more of the standard electrophysiological assays disclosed herein. Decreases of at least about 10% relative to baseline in the assay, preferably about 20% to 50% or more, are useful for many invention embodiments.

As will be appreciated, baseline values will often vary with respect to the particular polynucleotide(s) chosen. Methods to quantify baseline expression or protein include western blot, quantitative PCR, or functional assays such as adenylate cyclase assay for inhibitory G proteins, patch clamp analysis for ion channel currents. EP effects can be determined by measuring heart rate, conduction velocity or refractory period in vivo with EP catheters.

Additionally preferred invention methods include administration routes in which expression of the introduced polynucleotide directly or indirectly results in an increase in the AV node refractory period (AVNERP) as measured by the assay. An increase of at least about 10% relative to baseline in the assay, preferably at least about 20% to about 50% or more, will be preferred in many invention embodiments. Conventional methods for detecting and measuring the AVNERP are known and include the standard electrophysiological tests referenced herein.

Further preferred administation routes according to the invention involve introducing the polynucleotide into cardiac tissue and expressing same sufficient to detectably decrease heart rate as determined by a standard electrocardiogram (ECG) recording. Preferably, the decrease in heart rate is at least about 5% relative to baseline. Also preferably, the decrease in ventricular response rate or pulse during the cardiac arrhythmia (eg., atrial fibrillation) is at least about 10% relative to baseline as determined by the recording.

As will be apparent, the invention is highly flexible and can be used with one or a combination of polynucleotides, preferably those encoding at least one therapeutic heart protein. A more preferred polynucleotide: 1) either decreases the A-H interval or increases the AVNERP by at least about 10%, preferably at least about 20% to about 50%, as determined by the electrophysiological assay; and 2) decreases ventricular response rate or pulse rate during atrial fibrillation by at least about 10%, preferably at least about 20% to about 50% as determined by a standard electrocardiogram (ECG) recording.

Additionally preferred polynucleotides include, but are not limited to, those encoding at least one ion channel protein, gap junction protein, G protein subunit, connexin; or functional fragment thereof. More preferred are polynucleotides encoding a K channel subunit, Na channel subunit, Ca channel subunit, an inhibitory G protein subunit; or a functional fragment thereof. Additionally preferred polynucleotides will encode one, two or three of such proteins (the same or different). However polynucleotides encoding one of those proteins will be preferred for most invention applications.

By the phrase "function fragment" is meant a portion of an amino acid sequence (or polynucleotide encoding that sequence) that has at least about 80%, preferably at least about 95% of the function of the corresponding fall-length amino acid sequence (or polynucleotide encoding that sequence). Methods of detecting and quantifying functionality in such fragments are known and include the standard electrophysiological assays disclosed herein.

For example, in embodiments in one or more of the polynucleotides encodes an inhibitory G protein, a suitable test for assaying function of that protein (as well as functional fragments thereof) is the adenylate cyclase assay disclosed by Sugiyama A. et al. in *J Cardiovasc Pharm* 1997; 29:734.

Suitable polynucleotides for practicing the invention can be obtained from a variety of public sources including, but not limited to, GenBank (National Center for Biotechnology Information (NCBI)), EMBL data library, SWISS-PROT (University of Geneva, Switzerland), the PIR-International database; and the American Type Culture Collection (ATCC) (10801 University Boulevard, Manassas, Va. 20110-2209). See generally Benson, D. A. et al. (1997) *Nucl. Acids. Res.* 25: 1 for a description of Genbank.

More particular polynucleotides for use with the present invention are readily obtained by accessing public information from GenBank. For example, in one approach, a desired polynucleotide sequence is obtained from GenBank. The polynucleotide itself can be made by one or a combination of routine cloning procedures including those employing PCR-based amplification and cloning techniques. For example, preparation of oligonucleotide sequence, PCR amplification of appropriate libraries, preparation of plasmid DNA, DNA cleavage with restriction enzymes, ligation of DNA, introduction of DNA into a suitable host cell, culturing the cell, and isolation and purification of the cloned polynucleotide are known techniques. See eg., Sambrook et al. in *Molecular Cloning: A Laboratory Manual* (2d ed. 1989); and Ausubel et al. (1989), *Current Protocols in Molecular Biology*, John Wiley & Sons, New York.

Table 1 below, references illustrative polynucleotides from the GenBank database for use with the present invention.

TABLE 1

| Polynucleotide | GenBank Accession No. |
| --- | --- |
| Human Gi2 protein alpha subunit sequence: | AH001470 |
| Kir 2.1 potassium channel | XM028411[1] |
| HERG potassium channel | XM004743 |
| Connexin 40 | AF151979 |
| Connexin 43 | AF151980 |
| Connexin 45 | U03493 |
| Na channel alpha subunit | NM000335 |
| Na channel beta-1 subunit | NM001037 |
| L-type Ca channel alpha-1 subunit | AF201304 |

[1] An additional polynucleotide for use with the present invention is the Kir2.1 AAA mutant, which is wild-type Kir 2.1 with a substitution mutation of AAA for GFG in position 144–146.

Additional polynucleotides for use with the invention have been reported in the following references: Wong et al. *Nature* 1991;351(6321):63 (constitutively active Gi2 alpha); ) De Jongh K S, et al. *J Biol Chem* 1990 Sep. 5;265(25):14738 (Na and Ca channel beta subunits); Perez-Reyes, E. et al. *J Biol Chem* 1992 Jan. 25;267(3):1792; *Neuroscientist* 2001 February;7(1):42 (providing sodium channel beta subunit information); Isom, L L. Et al. *Science* 1992 May 8;256(5058):839 providing the beta 1 subunit of a brain sodium channel); and Isom, L L. Et al. (1995) *Cell* 1995 Nov. 3;83(3):433 (reporting beta 2 subunit of brain sodium channels).

Further polynucleotides for use with the invention have been reported in PCT application number PCT/US98/23877 to Marban, E.

See also the following references authored by E. Marban: J. Gen Physiol. 2001 August;118(2):171–82; Circ Res. 2001 Jul. 20;89(2):160–7; Circ Res. 2001 Jul. 20;89(2):101; Circ Res. 2001 Jul. 6;89(1):33–8; Circ Res. 2001 Jun. 22;88(12): 1267–75; J Biol Chem. 2001 Aug. 10;276(32):30423–8; Circulation. 2001 May 22;103(20):2447–52; Circulation. 2001 May 15;103(19):2361–4; Am J Physiol Heart Circ Physiol. 2001 June;280(6):H2623–30; Biochemistry. 2001 May 22;40(20):6002–8; J Physiol. 2001 May 15;533(Pt 1):127–33; Proc Natl Acad Sci U S A. 2001 Apr. 24;98(9): 5335–40; Circ Res. 2001 Mar. 30;88(6):570–7; Am J Physiol Heart Circ Physiol. 2001 April;280(4):H1882–8; and J Mol Cell Cardiol. 2000 November;32(11):1923–30.

Further examples of suitable Ca channel subunits include beta 1, or alpha2-delta subunit from an L-type Ca channel. A preferred Na channel subunit is beta1 or beta2. In some invention embodiments it will be useful to select Na and Ca channel subunits having having dominant negative activity as determined by the standard electrophysiological assay described below. Preferably, that activity suppresses at least about 10% of the activity of the corresponding normal Na or Ca channel subunit as determined in the assay.

Also preferred is the inhibitory G protein subunit ("$G\alpha_{i2}$") or a functional fragment thereof.

The invention is broadly suited for use with gap junction proteins, especially those known or suspected to be involved with cardiac function. Particular examples include connexin 40, 43, 45; as well as functional fragments thereof. Further contemplated are polynucleotides that encode a connexin having dominant negative activity as determined by the assay, preferably a suppression activity of at least about 10% with respect to the corresponding normal connexin 40, 43, or 45.

Also envisioned are mutations of such polynucleotides that encode dominant negative proteins (muteins) that have detectable suppressor activity. Encoded proteins that are genetically dominant typically inhibit function of other proteins particularly those proteins capable of forming binding complexes with the wild-type protein.

Additional polynucleotides of the invention encode essentially but not entirely full-length protein. That is, the protein may not have all the components of a full-length sequence. For example, the encoded protein may include a complete or nearly complete coding sequence (cds) but lack a complete signal or poly-adenylation sequence. It is preferred that a polynucleotide and particularly a cDNA encoding a protein of the invention include at least a complete cds. That cds is preferably capable of encoding a protein exhibiting a molecular weight of between about 0.5 to 70, preferably between about 5 and 60, and more preferably about 15, 20, 25, 30, 35, 40 or 50 kD. That molecular weight can be readily determined by suitable computer-assisted programs or by SDS-PAGE gel electrophoresis.

Although generally not preferred, the nucleic acid segment can be a genomic sequence or fragment thereof comprising one or more exon sequences. In this instance it is preferred that the cell, tissue or organ selected for performing somatic cell gene transfer be capable of correctly splicing any exon sequences so that a full-length or modified protein can be expressed.

The polynucleotide and particularly the cDNA encoding the full-length protein can be modified by conventional recombinant approaches to modulate expression of that protein in the selected cells, tissues or organs.

More specifically, suitable polynucleotides can be modified by recombinant methods that can add, substitute or delete one or more contiguous or non-contiguous amino acids from that encoded protein. In general, the type of modification conducted will relate to the result of expression desired.

For example, a cDNA polynucleotide encoding a protein of interest such as an ion channel can be modified so as overexpress that protein relative to expression of the full-length protein (i.e. control assay). Typically, the modified protein will exhibit at least 10 percent or greater overexpression relative to the full-length protein; more preferably at least 20 percent or greater; and still more preferably at least about 30, 40, 50, 60, 70, 80, 100, 150, or 200 percent or greater overexpression relative to the control assay.

As noted above, further contemplated modifications to a polynucleotide (nucleic acid segment) and particularly a cDNA are those which create dominant negative proteins.

In general, a variety of dominant negative proteins can be made by methods known in the field. For example, ion channel proteins are recognized as one protein family for which dominant negative proteins can be readily made, e.g., by removing selected transmembrane domains. In most cases, the function of the ion channel binding complex is substantially reduced or eliminated by interaction of a dominant negative ion channel protein.

Several specific strategies have been developed to make dominant negative proteins. Exemplary of such strategies include oligonucleotide directed and targeted deletion of cDNA sequence encoding the desired protein. Less preferred methods include nucleolytic digestion or chemical mutagenesis of the cDNA.

It is stressed that creation of a dominant negative protein is not synonymous with other conventional methods of gene manipulation such as gene deletion and antisense RNA. What is meant by "dominant negative" is specifically what is sometimes referred to as a "poison pill" which can be driven (i.e. expressed) by an appropriate DNA construct to produce a dominant negative protein which has capacity to inactivate an endogenous protein.

For example, in one approach, a cDNA encoding a protein comprising one or more transmembrane domains is modified so that at least 1 and preferably 2, 3, 4, 5, 6 or more of the transmembrane domains are eliminated. Preferably, the resulting modified protein forms a binding complex with at least one other protein and usually more than one other protein. As noted, the modified protein will inhibit normal function of the binding complex as assayed, e.g., by standard ligand binding assays or electrophysiological assays as described herein. Exemplary binding complexes are those which participate in electrical charge propagation such as those occurring in ion channel protein complexes. Typically, a dominant negative protein will exhibit at least 10 percent or greater inhibition of the activity of the binding complex; more preferably at least 20 percent or greater; and still more preferably at least about 30, 40, 50, 60, 70, 80, or 100 percent or greater inhibition of the binding complex activity relative to the full-length protein.

As a further illustration, a cDNA encoding a desired protein for use in the present methods can be modified so that at least one amino acid of the protein is deleted. The deleted amino acid(s) can be contiguous or non-contiguous deletions essentially up to about 1%, more preferably about 5%, and even more preferably about 10, 20, 30, 40, 50, 60, 70, 80, or 95% of the length of the full-length protein sequence.

Alternatively, the cDNA encoding the desired protein can be modified so that at least one amino acid in the encoded protein is substituted by a conservative or non-conservative amino acid. For example, a tyrosine amino acid substituted with a phenylalanine would be an example of a conservative amino acid substitution, whereas an arginine replaced with an alanine would represent a non-conservative amino acid substitution. The substituted amino acids can be contiguous or non-contiguous substitutions essentially up to about 1%, more preferably about 5%, and even more preferably about 10, 20, 30, 40, 50, 60, 70, 80, or 95% of the length of the full-length protein sequence.

Although generally less-preferred, the nucleic acid segment encoding the desired protein can be modified so that at least one amino acid is added to the encoded protein. Preferably, an amino acid addition does not change the ORF of the cds. Typically, about 1 to 50 amino acids will be added to the encoded protein, preferably about 1 to 25 amino acids, and more preferably about 2 to 10 amino acids. Particularly preferred addition sites are at the C- or N-terminus of the selected protein.

Preferred invention practice involves administering at least one of the foregoing polynucleotides with a suitable a myocardium nucleic acid delivery system. In one embodiment, that system includes a non-viral vector operably linked to the polynucleotide. Examples of such non-viral vectors include the polynucleoside alone or in combination with a suitable protein, polysaccharide or lipid formulation.

Additionally suitable myocardium nucleic acid delivery systems include viral vector, typically sequence from at least one of an adenovirus, adenovirus-associated virus (AAV), helper-dependent adenovirus, retrovirus, or hemagglutinating virus of Japan-liposome (HVJ) complex. Preferably, the viral vector comprises a strong eukaryotic promoter operably linked to the polynucleotide eg., a cytomeglovirus (CMV) promoter.

Additionally preferred vectors include viral vectors, fusion proteins and chemical conjugates. Retroviral vectors include moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex I virus (HSV) vector [Geller, A. I. et al., *J. Neurochem,* 64: 487 (1995); Lim, F., et al., in DNA Cloning: *Mammalian Systems,* D. Glover, Ed. (Oxford Univ. Press, Oxford England) (1995); Geller, A. I. et al., *Proc Natl. Acad. Sci.*: U.S.A.:90 7603 (1993); Geller, A. I., et al., *Proc Natl. Acad. Sci USA:* 87:1149 (1990)], Adenovirus Vectors [LeGal LaSalle et al., *Science,* 259:988 (1993); Davidson, et al., *Nat. Genet* 3:219 (1993); Yang, et al., *J. Virol.*69:2004 (1995)] and Adeno-associated Virus Vectors [Kaplitt, M. G., et al., *Nat. Genet.*8:148 (1994)].

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are may be indication for some invention embodiments. The adenovirus vector results in a shorter term expression (eg., less than about a month ) than adeno-associated virus, in some embodiments, may exhibit much longer expression. The particular vector chosen will depend upon the target cell and the condition being treated. Preferred in vivo or ex vivo cardiac administration techniques have already been described.

To simplify the manipulation and handling of the polynucleotides described herein, the nucleic acid is preferably inserted into a cassette where it is operably linked to a promoter. The promoter must be capable of driving expression of the protein in cells of the desired target tissue. The selection of appropriate promoters can readily be accomplished. Preferably, one would use a high expression promoter. An example of a suitable promoter is the 763-base-pair cytomegalovirus (CMV) promoter. The Rous sarcoma virus (RSV) (Davis, et al., *Hum Gene Ther* 4:151 (1993)) and MMT promoters may also be used. Certain proteins can expressed using their native promoter. Other elements that can enhance expression can also be included such as an enhancer or a system that results in high levels of expression such as a tat gene and tar element. This cassette can then be inserted into a vector, e.g., a plasmid vector such as pUC118, pBR322, or other known plasmid vectors, that includes, for example, an *E. coli* origin of replication. See, Sambrook, et al., *Molecular Cloning: A Laboratory Manual*, Cold Spring Harbor Laboratory press, (1989). The plasmid vector may also include a selectable marker such as the β-lactamase gene for ampicillin resistance, provided that the marker polypeptide does not adversely effect the metabolism of the organism being treated. The cassette can also be bound to a nucleic acid binding moiety in a synthetic delivery system, such as the system disclosed in WO 95/22618.

If desired, the polynucleotides of the invention may also be used with a microdelivery vehicle such as cationic liposomes and adenoviral vectors. For a review of the procedures for liposome preparation, targeting and delivery of contents, see Mannino and Gould-Fogerite, *BioTechniques*, 6:682 (1988). See also, Felgner and Holm, *Bethesda Res. Lab. Focus,* 11(2):21 (1989) and Maurer, R. A., *Bethesda Res. Lab. Focus,* 11(2):25 (1989).

Replication-defective recombinant adenoviral vectors, can be produced in accordance with known techniques. See, Quantin, et al., *Proc. Natl. Acad. Sci. USA,* 89:2581–2584 (1992); Stratford-Perricadet, et al., *J. Clin. Invest.,* 90:626–630 (1992); and Rosenfeld, et al., *Cell,* 68:143–155 (1992).

The effective dose of the nucleic acid will be a function of the particular expressed protein, the particular cardiac arrhythmia to be targeted, the patient and his or her clinical condition, weight, age, sex, etc.

One preferred myocardicum delivery system is a recombinant viral vector that incorporates one or more of the polynucleotides therein, preferably about one polynucleotide. Preferably, the viral vector used in the invention methods has a pfu (plague forming units) of from about $10^8$ to about $5\times10^{10}$ pfu. In embodiments in which the polynucleotide is to be administered with a non-viral vector, use of between from about 0.1 nanograms to about 4000 micrograms will often be useful eg., about 1 nanogram to about 100 micrograms.

Choice of a particular myocardium delivery system will be guided by recognized parameters including the cardiac arrhythmia of interest and the amount and length of expression desired. Use of virus vectors approved for human applications eg., adenovirus are particularly preferred.

As discussed, it is an object of the invention to prevent or treat cardiac arrhythmia. In one embodiment, the method further includes overexpressing a potassium (K) channel protein subunit sufficient to decrease cardiac action potential duration (APD) by at least about 5% as determined by the standard cardiac electrophysiological assay.

Reference herein to an electrophysiological assay is meant a conventional test for determining cardiac action potential (AP). See generally Fogoros R N. *Electrophysiologic Testing* Blackwell Science, Inc. (1999.) for disclosure relating to performing such tests.

Specific reference herein to a "standard electrophysiological assay" is meant the following general assay.

1) providing a mammalian heart (in vivo or ex vivo),
2) contacting the heart with at least one suitable polynucleotide preferably in combination with an appropriate myocardium nucleic acid delivery system,
3) transferring the polynucleotide into cells of the heart under conditions which allow expression of the encoded amino acid sequence; and
4) detecting modulation (increase or decrease) of at least one electrical property in the transformed heart eg., at least one of conduction, ventricular response rate, and pulse rate.

Particular invention methods include modifying the polynucleotide along lines discussed above sufficient to overexpress the encoded protein. Further preferred are methods in which the nucleic acid is modified to produce a dominant negative ion channel protein. The ion channel protein can be e.g., a sodium, calcium, voltage-gated, or ligand-gated ion channel and particularly a potassium ion channel. Additional disclosure relating to such channel proteins can be found in the discussion above and in U.S. Pat. No. 5,436,128, for instance.

Practice of the invention is broadly compatible with one or a combination of different administration (delivery) systems.

In particular, one suitable administration route involves one or more appropriate polynucleotide into myocardium. Alternatively, on in addition, the administration step includes perfusing the polynucleotide into cardiac vasculature. If desired, the administration step can further include increasing microvascular permeability using routine procedures, typically administering at least one vascular permeability agent prior to or during administration of the gene transfer vector. Examples of particular vascular permeability agents include administration of one or more of the following agents preferably in combination with a solution having less than about 500 micromolar calcium: substance P, histamine, acetylcholine, an adenosine nucleotide, arachidonic acid, bradykinin, endothelin, endotoxin, interleukin-2, nitroglycerin, nitric oxide, nitroprusside, a leukotriene, an oxygen radical, phospholipase, platelet activating factor, protamine, serotonin, tumor necrosis factor, vascular endothelial growth factor, a venom, a vasoactive amine, or a nitric oxide synthase inhibitor. A particular is serotonin, vascular endothelial growth factor (VEGF), or a functional VEGF fragment to increase the permeability.

Typical perfusion protocols in accord with the invention are generally sufficient to transfer the polynucleotide to at least about 10% of cardiac myocytes in the mammal. Infusion volumes of betweeen from about 0.5 to about 500 ml are preferred. Also preferred are coronary flow rates of between from about 0.5 to about 500 ml/min. Additionally perfered perfusion protocols involve the AV nodal artery. Transformed heart cells, typically cardiac myocytes that include the polynucleotide are suitably positioned at or near the AV node.

Illustrative strategies for detecting modulation of transformed heart have been disclosed eg., in Fogoros R N, supra. A preferred detection strategy is performing a conventional electrocardiogram (ECG). Modulation of cardiac electrical properties by use of the invention is readily observed by inspection of the ECG. See also the Examples and Drawings below.

More specific methods for preventing or treating cardiac arrhythmia include overexpressing a K channel protein subunit sufficient to decrease surface electrocardiogram (ECG) repolarization time by at least about 5%, preferably at least about 10% to about 20%, as determined by the assay. Typically, the K channel protein subunit is overexpressed by at least about 2 fold, preferably about 5 fold, relative to an endogenous K channel protein as determined by a standard Northern or Western blot assay. Also preferably, the K channel protein subunit is overexpressed and impacts repolarization in congestive heart failure or myocardial infarction in the long QT syndrome.

In particular embodiments, methods for preventing or treating cardiac arrhythmia provided herein further include decreasing conduction through cardiac tissues by at least about 5%, preferably at least about 10% to about 20%, as determined by the standard electrophysiological assay.

As discussed, the invention is one of general application that can be used one or a combination of different cardiac arrhythmias. Examples of particular arrhythmias has been disclosed by Bigger, J. T and B. F. Hoffman, supra. More specific examples include atrial flutter, atrial fibrillation, and ventricular tachycardia. Other examples include sinus bradycardia, sinus tachycardia, atrial tachycardia, atrial fibrillation, atrial flutter, atrioventricular nodal block, atrioventricular node reentry tachycardia, atrioventricular reciprocating tachycardia, ventricular tachycardia or ventricular fibrillation.

The following sections 1–5 discuss particular uses of the present invention.

1. Sinus Bradycardia: Direct injection or intravascular perfusion of materials/vectors into the atria or ventricles in order to create a discrete focus of electrically active tissue to replace the function of the sinus node. Indications might include: sick sinus syndrome, Stokes-Adams attacks, syncope, chronic fatigue syndrome, cardiomyopathies (hypertrophic and dilated), and all other present and future indications for electronic pacemakers. Therapeutic genes could include wild-type or mutated potassium, HCN and/or calcium channel subunits to increase local automaticity and/or to induce pacemaker activity where it is not normally present.
2. Inappropriate Sinus Tachycardia: Modification of the automaticity in the sinus node and/or surrounding atrial tissue for the treatment of inappropriate sinus tachycardia, e.g. by introducing K channel, Ca channel or HCN channel genes to decrease nodal excitability
3. Atrial Fibrillation/Atrial Flutter/Atrial Tachycardia: Direct injection or intravascular perfusion of materials/vectors in order to: (1) produce lines of conduction block in order to prevent conduction of reentry-type atrial arrhythmias, (2) suppress automaticity or increase refractoriness in order to ablate discrete arrhythmic foci of tissue, (3) affect conduction velocity, refractoriness or automaticity diffusely throughout the atria in order to prevent or treat atrial fibrillation, multifocal atrial tachycardia or other atrial tachycardias with multiple or diffuse mechanisms, or (4) Direct injection into the atrioventricular node or perfusion of the atrioventricular nodal artery with materials/vectors to alter the conduction properties (conduction velocity, automaticity, refractoriness) of the atrioventricular node in order to slow the ventricular response rate to atrial arrhythmias.
4. Atrioventricular nodal block: Direct injection or intracoronary perfusion of materials/vectors into the atrioventricular nodal region or into the ventricles in order to (1) create a discrete focus of electrically active tissue to initiate the heart beat in the absence of atrioventricular nodal conduction of the normal impulse from the atria, or (2) reestablish function of the atrioventricular node.
5. Ventricular Tachycardia/Ventricular Fibrillation: Delivery of vectors by: (1) Direct injection into discrete foci of ventricular myocardium to suppress automaticity or increase refractoriness in order to ablate arrhythmic foci by genetic means, (2) Diffuse direct injection or coronary artery perfusion of materials/vectors into both ventricles to affect the conduction properties (conduction velocity, automaticity, refractoriness) of ventricular tissue in order to treat or prevent ventricular arrhythmias, or (3) Direct injection of materials/vectors to produce lines of conduction block in order to prevent conduction of reentry-type ventricular arrhythmias.

As also discussed, the present invention provides more specific methods for preventing or treating ventricular rate or pulse during atrial fibrillation. In one embodiment, the method includes administering to the mammal a therapeutically effective amount of at least one polynucleotide encoding a $G\alpha_{i2}$ subunit or a functional fragment thereof. Typically preferred methods further include expressing the polynucleotide in the mammal to prevent or treat the atrial fibrillation. Preferred methods also include overexpressing the $G\alpha_{i2}$ subunit or a functional fragment thereof sufficient to decrease speed of conduction through the atrioventricular (AV) node (A-H interval) or His-Purkinje system as determined by a standard electrophysiological assay. Also preferably, the decrease in the A-H interval is accompanied by an increase in AV node refractory period (AVNERP). The decrease in the A-H interval is at least about 10%, preferably at least about 20%, as determined by the assay. The increase in AVNERP is at least about 10%, preferably at least about 20%, as determined by the assay.

By the phrase "therapeutically effective" amount or related phrase is an amount of administered polynucleotide needed to achieve a desired clinical outcome.

In one embodiment of the foregoing specific method, overexpression of the $G\alpha_{i2}$ or a functional fragment thereof is capable of decreasing pulse rate or ventricular rate during atrial fibrillation as determined by a standard cardiac electrophysiological assay. Preferably, the decrease in pulse rate or ventricular rate during atrial fibrillation is at least about 10%, preferably at least about 20%, as determined by the assay.

The foregoing embodiment of the invention for preventing or treating atrial fibrillation provides specific advantages. For example, it has been found that it is possible to transfer genes to half of AV nodal cells with clinically relevant delivery parameters. Desirable therapeutic effects of the gene therapy include slowing of AV nodal conduction and increases of the refractory period of the AV node, with resultant slowing of the ventricular response rate during atrial fibrillation. The work provides proof of principle that gene therapy is a viable option for the treatment of common arrhythmias.

In one invention embodiment, the polynucleotide encoding the $G\alpha_{i2}$ subunit hybridizes to the nucleic acid sequence shown in FIGS. 9B–C (SEQ ID NO's: 1–9, repectively in order of appearance); or the complement thereof under high stringency hybridization conditions. Encoded amino acid sequence is shown in FIG. 9A (SEQ ID NO: 10). By the phrase "high stringency" hybridization conditions is meant nucleic acid incubation conditions approximately 65° C. in 0.1×SSC. See Sambrook, et al., infra. Preferably, the polynucleotide consists of or comprises the nucleic acid shown in FIGS. 9B–C (SEQ ID NO's: 1–9, respectively in order of appearance). FIGS. 9A–C show the subunit nucleotide sequence as exon representations. It will be appreciated that in the gene sequence, the exons are covalently linked together end-to-end (exon 1, 2, etc)

As discussed, it is an object of the present invention to use gene therapy as an antiarrhythmic strategy. The Examples section, in particular, focuses genetic modification of the AV node. An intracoronary perfusion model for gene delivery, building on previous work in isolated cardiac myocytes and ex vivo-perfused hearts has been developed.[4,5]. Using this method, porcine hearts were infected with Adβgal (a recombinant adenovirus expressing *E. coli* β-galactosidase) or with AdG$_i$ (encoding the Gα$_{i2}$ subunit). Gα$_{i2}$ overexpression suppressed baseline AV conduction and slowed the heart rate during atrial fibrillation, without producing complete heart block. In contrast, expression of the reporter gene β-galactosidase had no electrophysiological effects. These results demonstrate the feasibility of using myocardial gene transfer strategies to treat common arrhythmias.

More generally, the invention can be used to deliver and express a desired ion channel, extracellular receptor, or intracellular signaling protein gene in selected cardiac tissues, particularly to modify the electrical properties of that tissue, e.g., increasing or decreasing its refractoriness, increasing or decreasing the speed of conduction, increasing or decreasing focal automaticity, and/or altering the spatial pattern of excitation. The general method involves delivery of genetic materials (DNA, RNA) by injection of the myocardium or perfusion through the vasculature (arteries, veins) or delivery by nearly any other material sufficient to facilitate tranformation into the targeted portion of the myocardium using viral (adenovirus, AAV, retrovirus, HVJ, other recombinant viruses) or non-viral vectors (plasmid, liposomes, protein-DNA combinations, lipid-DNA or lipid-virus combinations, other non-viral vectors) to treat cardiac arrhythmias.

By way of illustration, genes that could be used to affect arrhythmias include ion channels and pumps (α subunits or accessory subunits of the following: potassium channels, sodium channels, calcium channels, chloride channels, stretch-activated cation channels, HCN channels, sodium-calcium exchanger, sodium-hydrogen exchanger, sodium-potassium ATPase, sarcoplasmic reticular calcium ATPase), cellular receptors and intracellular signaling pathways (α or β-adrenergic receptors, cholinergic receptors, adenosine receptors, inhibitory G protein α subunits, stimulatory G protein α subunits, Gβγ subunits) or genes for proteins that affect the expression, processing or function processing of these proteins.

Selection of the appropriate gene(s) for therapy can be performed by anyone with an elementary knowledge of cardiac electrophysiology. In addition, the effects of ion channel expression can be simulated by computer programs to anticipate the effects of gene transfer. The delivery methods for myocardial delivery are widely reported, and methods involving injection of the myocardium or intravascular perfusion have been used successfully.

More specific advantages of the invention include ability to convey localized effects (by focal targeted gene delivery), reversible effects (by use of inducible vectors, including those already reported as well as new generations of such vectors, including but not limited to adeno-associated vectors using tetracycline-inducible promoters to express wild-type or mutant ion channel genes), gradedness (by use of inducible vectors as noted above, in which gradedness would be achieved by titration of the dosage of the inducing agent), specificity of therapy based on the identity of the gene construct, ability to regulate therapeutic action by endogenous mechanisms (nerves or hormones) based on the identity of the gene construct, and avoidance of implantable hardware including electronic pacemakers and AICDs, along with the associated expense and morbidity.

Figures 8A, 8B:
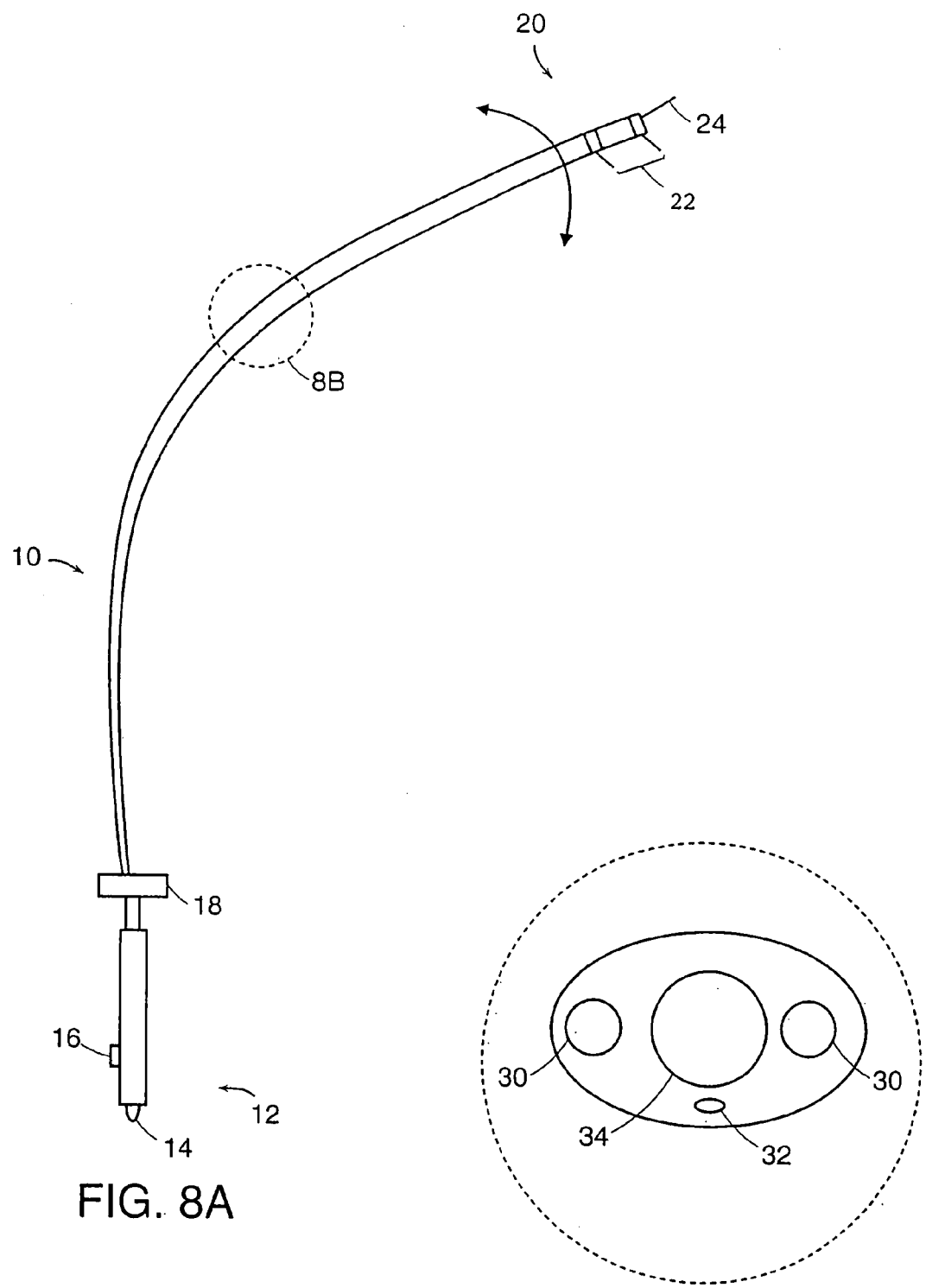
FIGS. 8A and 8B depict a preferred therapeutic agent delivery device (intravascular injection catheter) of the invention.

As discussed above, the invention also includes devices useful in the treatment methods of the invention. These devices include catheters that include in a single unitary unit that contain both delivery and position detection features. FIGS. 8A and 8B show catheter unit 10 that contains at proximal end 12 (i.e. end manipulated by medical practitioner, typically external to patient) electrical connection 14, therapeutic agent injection port and needle extension mechanism 16, and steering control 18. Distal end 20 of catheter 10 includes electrodes 22 for detection of the distal end position within a patient and retractable needle 24 for delivery of the therapeutic agent, particularly a polynucleotide to targeted tissue, especially a polynucleotide to mammalian cardiac tissue. The needle 24 can be manipulated by extension mechanism 16. Connection 14 enables activation of detection apparatus 22. A therapeutic agent such as a polynucleotide can be injected or otherwise introduced into device 10 via injection port 16. FIG. 8B shows the specified catheter region in cross-section with electrode cables 30 that provide communication between electrical connection 14 and electrodes 22, steering rod 32 that can enable manipulation of catheter 10 within the patient via steering control 14, and injector connection or tubing 34 that provides a path for delivery of the therapeutic agent through catheter 10 to the targeted tissue of the patient. The device is suitably employed in a minimally invasive (endoscopic) procedure.

Variations of the depicted design also will be suitable. For instance, the catheter may comprise a tip (distal portion) with a fixed curve. Additionally, rather than having the therapeutic agent traverse the catheter 10, the agent may be housed within a reservoir, which may be activated (i.e. therapeutic agent released to patient) via mechanism at catheter proximal end. The needle 24 may be a straight needle or a screw-type apparatus. In each design, the device suitable contains some type of detection apparatus, e.g. electrodes that provide for electrophyiologically-guided substance injections into the targeted tissue.

The following specific examples are illustrative of the invention.

EXAMPLE 1

Gene Transfer of β-galactosidase (β-gal) and Inhibitory G Protein Subunit (Gα$_{i2}$) Into Cardiac Tissue In previous ex vivo and in vitro studies, we found that gene transfer efficiency correlated with coronary flow rate, virus exposure time, virus concentration, and the level of microvascular permeability[4,5]. We also found that elimination of radiographic contrast media and red blood cells from the perfusate and delivery at body temperature were necessary for optimal results. The in vivo delivery system used in this report builds on those findings.

Ten animals underwent a protocol that included medication with oral sildenafil before baseline electrophysiology (EP) study, catheterization of the right coronary artery, and infusion of VEGF, nitroglycerin and virus-containing solutions (7.5×10$^9$ pfu in 1 ml) into the AV nodal branch of the right coronary artery. VEGF was used to increase microvascular permeability[6], and sildenafil potentiated the VEGF effect. The infusion volume and coronary flow rate were limited to avoid efflux from the artery and infection of other regions of the heart. Five animals received Adβgal, and the other 5 received AdG$_i$. The animals underwent follow-up EP study 7 days after virus infusion. After the second EP study, the hearts were explanted and evaluated for β-galactosidase (β-gal) and Gα$_{i2}$ expression. Other adenoviral gene transfer studies have shown that expression is detectable after 3 days, peaks after 5–7 days, and then regresses over 20–30 days[7–9].

Based on these data, we tested for gene expression and phenotypic changes 7 days after gene delivery.

X-gal staining revealed β-gal activity in the AV nodal region and adjacent ventricular septum of all Adβgal-infected animals (FIG. 1a). There was no evidence of β-gal activity in any of the AdG$_i$-infected animals or in other heart sections from the Adβgal group. Microscopic sections through the AV node documented gene transfer to 45±6% of the AV nodal cells in the Adβgal group and confirmed the absence of X-gal staining in the AdG$_i$-infected animals. Also notable in the microscopic sections was a mild inflammatory infiltrate, comprised mainly of mononuclear cells.

Western blot analysis was performed on tissue homogenates from the AV nodal region of 4 animals from each group (FIG. 1b). Densitometry analysis confirmed Gα$_{i2}$ overexpression in the AdG$_i$ group, amounting to a 5-fold increase in Gα$_{i2}$ relative to the Adβgal animals (p=0.01). The level of Gα$_{i2}$ in the Adβgal group was not different from that found in 2 uninfected control animals.

X-gal staining of gross and microscopic sections from the lung, liver, kidney, skeletal muscle and ovaries of all animals was performed to evaluate the extent of gene transfer outside the heart (FIG. 1c). In the Adβgal-infected animals, β-gal activity was evident in gross specimens from the liver, kidneys and ovaries, but not in the lungs or skeletal muscle. Microscopic sections revealed definite β-gal activity, but in less than 1% of the cells in these organs. X-gal staining was not found in any tissues of the AdG$_i$-infected or uninfected control animals. The lack of X-gal staining in AdG$_i$-infected and uninfected controls indicates that the results were specific for transgene expression and not from endogenous β-gal activity or false-positive staining. These results are consistent with a previous study documenting gene expression in peripheral organs after intracardiac injection of adenovirus[10], and suggest that ongoing clinical gene therapy trials should consider the risks of non-target organ gene transfer.

FIGS. 1A–D are explained in more detail as follows. Measurement of gene transfer efficacy. FIG. 1. X-gal staining of a transverse section through the AV groove. Arrowheads indicate the tricuspid valve ring, and the solid arrow marks the central fibrous body. The hollow arrow points to the AV node. FIG. 1B. A microscopic section through the AV node shows gene transfer to 45±6% of myocytes. Cells expressing β-galactosidase are stained blue. FIG. 1C. Gross and microscopic pathology after exposure of liver, kidney and ovary to X-gal solution. FIG. 1D. Microscopic sections show rare blue cells in these organs (arrowheads). Lung and skeletal muscle failed to show any evidence of gene transfer.

EXAMPLE 2

Electrophysiological Analysis of Cardiac Tissue Transduced with β-gal or Inhibitory G Protein (Gα$_{i2}$) Subunit Electrophysiological measurements obtained at baseline and 7 days after infection are displayed in Table 2, below.

TABLE 2

Electrophysiological Parameters Before and 7 Days After Gene Transfer

| | Adβgal | | AdG$_i$ | |
|---|---|---|---|---|
| Day | 0 | 7 | 0 | 7 |
| Heart rate during sinus rhythm | 114 ± 5 | 111 ± 1 | 113 ± 2 | 106 ± 4 |
| ECG: P-R interval | 101 ± 1 | 99 ± 1 | 97 ± 2 | 109 ± 5* |
| QRS interval | 58 ± 2 | 54 ± 1 | 57 ± 1 | 56 ± 1 |

TABLE 2-continued

Electrophysiological Parameters Before and 7 Days After Gene Transfer

| | Adβgal | | AdG$_i$ | |
|---|---|---|---|---|
| Day | 0 | 7 | 0 | 7 |
| Q-T interval | 296 ± 6 | 310 ± 2 | 288 ± 7 | 316 ± 6 |
| A-H interval | 61 ± 1 | 61 ± 1 | 60 ± 2 | 76 ± 3* |
| H-V interval | 25 ± 1 | 25 ± 1 | 23 ± 1 | 24 ± 1 |
| AVNERP | 226 ± 6 | 224 ± 4 | 226 ± 6 | 246 ± 3* | mean ± s.e.m., n = 5 in each group, * p ≤ 0.03; AVNERP: AV node effective refractory period ECG parameters were taken from the surface ECG, and the A-H and H-V intervals were recorded from an intracardiac catheter in the His-bundle position. (The A-H interval measures conduction time through the AV node, and the H-V interval is the conduction time through the His-Purkinje system.) The AV node effective refractory period (AVNERP) was measured by pacing the atria at a stable rate for 8 beats and then delivering premature atrial stimuli at progressively shorter intervals, noting the interval where the premature beat failed to conduct through the AV node. There were no significant differences in the electrophysiological parameters between groups at baseline. In the Adβgal group, comparison of baseline measurements to those taken 7 days after infection also failed to show any significant differences. In contrast, the follow-up study of the AdG$_i$ group revealed significant prolongation in the P–R interval on the surface ECG (paired analysis, day 0: 97±2 msec, day 7: 109±4 msec, p=0.01), the A-H interval on the intracardiac electrogram (day 0: 60±2 msec, day 7: 76±3 msec, p=0.01) and the AVNERP (day 0: 226±6 msec, day 7: 246±3 msec, p=0.03), indicating both slowed conduction and increased refractoriness of the AV node after Gα$_{i2}$ overexpression.

EXAMPLE 3

Measurement of Heart Rate in Cardiac Tissue Transduced with β-gal or Inhibitory G Protein (Gα$_{i2}$) Subunit After measurement of basic electrophysiological intervals, we measured the heart rate during acute episodes of atrial fibrillation. Overexpression of Gα$_{i2}$ in the AV node caused a 20% reduction in the ventricular rate during atrial fibrillation (day 0: 199±5 bpm, day 7: 158±2 bpm, p=0.005). This effect persisted in the setting of adrenergic stimulation. Administration of epinephrine (1 mg, IV) increased the atrial fibrillation heart rate in all animals, but the group overexpressing Gα$_{i2}$, nevertheless, exhibited a 16% reduction in ventricular rate (day 0: 364±3 bpm, day 7: 308±2 bpm, p=0.005). In contrast, β-gal expression did not affect the heart rate during atrial fibrillation, either before (day 0: 194±8 bpm, day 7: 191±7 bpm, p=NS) or after epinephrine administration (day 0: 362±6 bpm, day 7: 353±5, p=NS).

To further evaluate the effect of Gα$_{i2}$ overexpression on AV conduction, we analyzed the heart rate at various time points after induction of atrial fibrillation in the AdG$_i$-epinephrine group. These data indicate that the ventricular rate remains stable and that the beneficial suppression of heart rate from Gα$_{i2}$ gene transfer is sustained through at least 3 minutes of observation. The episodes of atrial fibrillation often lasted longer than 3 minutes (see methods), but the period of observation was limited to ensure that the effects of epinephrine would be constant.

The choice of $G\alpha_{i2}$ to suppress conduction was inspired by the success of β-blocking drugs at achieving that goal. In the AV node, β-adrenergic receptors are coupled to stimulatory G proteins ($G_S$). Stimulation of β-receptors activates $G_S$, releasing the $G\alpha_S$-subunit to stimulate adenylate cyclase[11]. This process leads to a cascade of intracellular events causing an increase in conduction velocity and a shortening of the refractory period. β-blockers prevent the increase in AV nodal conduction by inhibiting receptor activation.

The intracellular processes responsive to $G_S$ are counterbalanced by the activity of inhibitory G proteins ($G_i$). In the AV node, $G_i$ are coupled to muscarinic M2 and adenosine A1 receptors[11]. $G_i$ activation releases the $G\alpha_i$-subunit to bind and inhibit adenylate cyclase activity and the Gβγ-subunit to increase potassium conductance by direct action on acetylcholine-activated potassium channels. The cumulative effect of $G_i$ activation is a decrease in conduction through the AV node. In agreement with these known effects of the G protein cascade, our data show that overexpression of $G\alpha_{i2}$ suppresses AV nodal conduction in the drug-free state and during adrenergic stimulation.

Under ordinary circumstances, $G\alpha_{i2}$-mediated inhibition of adenylate cyclase requires receptor activation[12]. In the current study, however, $G_i$ activity appears to be uncoupled from the receptor, since the inhibition occurs without exogenous M2 or A1 receptor stimulation. In the setting of 5-fold overexpression of $G\alpha_{i2}$, normal cellular mechanisms may well be altered. Further study will be required to elucidate the changes in signal transduction that underlie the observed effects.

A principal focus of this study was to overcome the problem of vector delivery to the myocardium using minimally invasive techniques. By manipulation of the tissue and vascular dynamics, the β-galactosidase and $G\alpha_{i2}$ genes were transferred to 45% of AV nodal myocytes by intracoronary catheterization. A limited inflammatory response was noted after adenoviral infection, but there was no detectable effect on AV nodal function from the inflammation or from reporter gene transfer. Other studies have shown that the use of first-generation adenoviruses (those with E1 deletions) leads to intense inflammation and loss of transgene expression 20–30 days after infection[13]. When used at high concentrations (much greater than those in this study), adenovirus vectors are also associated with endothelial damage, arterial thrombosis, thrombocytopenia, anemia, hepatitis, and death[14-17]. Wild-type adenoviruses have also been implicated in the development of myocarditis and idiopathic cardiomyopathy[18]. Since this study used a relatively low concentration of virus and looked at phenotypic changes early after gene transfer, these limitations did not affect the findings reported here.

This study is the first report of intracoronary site-specific gene transfer, as well as the first use of gene therapy to treat cardiac arrhythmias. We demonstrate that overexpression of an inhibitory component of the β-adrenergic signaling pathway suppresses AV nodal conduction, and also document the absence of electrophysiological changes after adenovirus-mediated transfer of a reporter gene. In summary, our research provides proof of the principle that in vivo gene transfer can modify the cardiac electrical substrate and lays the groundwork for future investigations to treat common arrhythmias.

FIGS. 2A–B and 3A–B are explained in more detail as follows. Reduction in heart rate during atrial fibrillation after $G\alpha_{i2}$ gene transfer. In the drug-free state, $G\alpha_{i2}$ overexpression reduces ventricular rate by 20% during atrial fibrillation. No difference in heart rate is observed after Adβgal exposure. After infusion of epinephrine (1 mg, IV), the relative effect of $G\alpha_{i2}$ overexpression persists (‡ p=0.005).

EXAMPLE 4

Heart Rate Control During Atrial Fibrillation

The present example shows conduction slowing and increased refractoriness.

Atrial fibrillation affects more than 2 million people in the United States, including 5–10% of people over the age of 65 and 10–35% of the 5 million patients with congestive heart failure. Treatment strategies for AF include antiarrhythmic therapy to maintain sinus rhythm or ventricular rate control and anticoagulation. Although appealing, the maintenance of sinus rhythm is often unsuccessful. Within 1 year of conversion to sinus rhythm, 25–50% of patients revert to AF in spite of antiarrhythmic drug treatment.[1] The usual clinical situation, then, is to maintain anticoagulation and ventricular rate control during chronic AF. The variable efficacy and frequent systemic adverse effects from rate controlling drugs motivated our development of animal models of gene transfer to control the heart rate in atrial fibrillation.

In porcine models of acute and chronic atrial fibrillation (AF), animals underwent coronary catheterization to deliver recombinant adenovirus to the atrioventricular nodal region of the heart. Immediately prior to catheterization, female domestic swine (30–40 kg) received sustained release diltiazem 180 mg, aspirin 325 mg and sildenafil 25 mg orally, and a mixture of ketamine 100 mg and acepromazine 4 mg intramuscularly. (For uniformity, the same pretreatment regimen, except administration of sildenafil, was used for all procedures to control for any effect these agents might have on the baseline EP measurements.) After sedation, anesthesia was induced with 5–10 ml of intravenous sodium pentothal 2.5% solution and maintained with inhaled isoflurane 2% in oxygen. The right carotid artery, right internal jugular vein and right femoral vein were accessed by sterile surgical technique, and introducer sheaths were inserted into each vessel. After baseline EP study, the right coronary artery was catheterized via the right carotid artery, using a 7 Fr. angioplasty guiding catheter. The AV nodal branch was selected with a 0.014" guide wire, over which a 2.7 Fr. infusion catheter was inserted into the AV nodal artery. The following solutions were infused through the catheter: 10 ml of normal saline (NS) containing 5 μg of $VEGF_{165}$ and 200 μg of nitroglycerin over 3 minutes, 1 ml of normal saline containing $7.5 \times 10^9$ pfu of AdGi or Adβgal and 20 μg of nitroglycerin over 30 seconds, and 2 ml of normal saline over 30 seconds. After recovery from anesthesia, the animals received usual care and no additional medication. After one week, repeat EP evaluation was performed; the animals were sacrificed, and the organs were removed for histological evaluation.

Oral treatment with sildenafil and infusion of VEGF, nitroglycerin and calcium-free solutions served to increase microvascular permeability and thus increase the efficiency of gene transfer. Using this delivery method, Western blot analysis demonstrated 600% overexpression of $G\alpha_{i2}$ in the AdGi group when compared to untreated or Adβgal-treated controls (FIG. 4A, p=0.01). The Adβgal-treated animals did not have significant differences in $G\alpha_{i2}$ expression when compared to controls.[2]

After gene transfer, the heart rate was determined at the 1 week follow-up EP study for animals with acutely-induced AF, and heart rate was determined daily for animals with chronic AF. The acute AF model emulates the human condition of paroxysmal AF. In the acute AF model, Heart rate during acutely induced atrial fibrillation was decreased by 20% in the AdGi-treated animals and unchanged in the Adβgal-treated animals when compared to the untreated state (FIG. 4B, p=0.005 for AdGi and p=NS for Adβgal compared to baseline).[2] In the chronic AF model, heart rate in the AdGi group decreased by 35% 7–10 days after gene transfer. There was no change in heart rate in the Adβgal group. This example shows that $G\alpha_{i2}$ overexpression is capable of reducing heart rate by 20–35% in acute and chronic models of AF. By comparison, currently available drug therapies reduce heart rate by 15–30%, but treatment is often limited by systemic side effects.[1]

FIGS. 4A–B are explained in more detail as follows. FIG. 4A. Western blot of AV nodal tissue demonstrates $Ga_{i2}$ overexpression in the $AdG_i$ infected animals. Lane 1 is 10 mg of $Ga_{i2}$ control. Lanes 2, 4, 6, 8 are from Adbgal-infected animals and lanes 3, 5, 7, 9 are from $AdG_i$-infected animals. Analysis of the bands shows a 5±1-fold increase in $Ga_{i2}$ content in the $AdG_i$ animals relative to the Adbgal-infected controls. FIG. 4B. Analysis of heart rate before and 7 days after gene transfer. AdGi gene transfer reduces ventricular rate by 20% during atrial fibrillation (p=0.005). No difference in heart rate was observed after Adbgal exposure.

EXAMPLE 5

Treatment of Polymorphic Ventricular Tachycardia in Congestive Heart Failure or the Long QT Syndrome Sudden death in patients with congestive heart failure is a common clinical occurrence. In most studies, roughly half of all heart failure deaths were sudden in nature. Often, the associated arrhythmia is polymorphic ventricular tachycardia (VT) leading to ventricular fibrillation and death. The type of VT seen in these patients is similar to that observed in patients with the congenital long QT syndrome. Studies of animal models have documented the similarities between these two diseases on a tissue and cellular level. In both conditions, heterogeneous increases in the action potential duration (APD) have been a consistent finding. In heart failure, the APD prolongation correlates with downregulation of several potassium currents: the transient outward current $I_{to}$, the inward rectifier current $I_{K1}$, and the delayed rectifier currents $I_{Ks}$ and $I_{Kr}$. In the long QT syndrome, prolongation of the action potential correlates with mutation in one of the potassium or sodium channel genes. Either condition disrupts the balance of inward and outward currents, predisposing the patient to malignant ventricular arrhythmias. This balance can be restored by gene transfer-induced overexpression of potassium channels.

In a guinea pig model, animals underwent surgical injection of AdHERG and then were followed for changes in APD and QT.[3] Adult guinea pigs (200–250 g) received metafane anesthesia. The abdominal wall was incised in sterile surgical fashion. The diaphragm was fixated with forceps in incised in an anterior-posterior direction. The pericardium was fixated and opened. The heart was fixated, and 0.15 ml of AdHERG containing solution was injected into multiple sites in the left ventricular free wall. The incisions were closed and the animal was allowed to recover. After 3 days, the animals were sacrificed and the cardiac myocytes were enzymatically isolated. Using conventional patch clamp methods, APD and ion channel currents were measured. In comparison to control animals, AdHERG-infected animals exhibited a 7-fold increase in $I_{Kr}$ outward current and a 50% reduction in APD. See FIGS. 5A–B.[3]

FIGS. 5A–B are explained in more detail as follows. FIG. 5A. Comparison of $I_{Kr}$ current in the presence or absence of gene transfer-mediated overexpression of HERG. FIG. 5B. Photograph of an action potential tracing from a cell overexpressing HERG.

EXAMPLE 6

Treatment of Atrial Fibrillation

Figure 6:
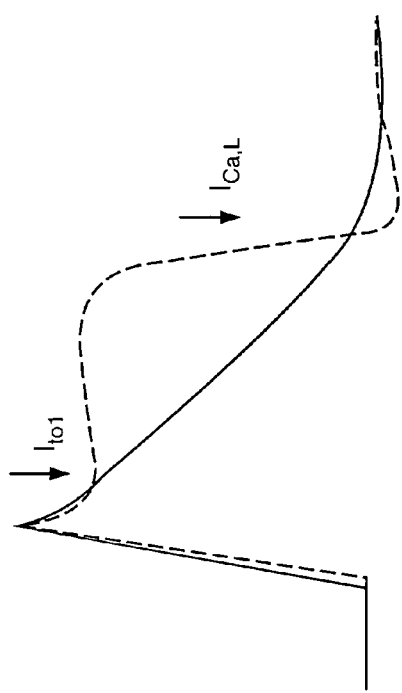
FIG. 6 is a drawing showing changes in atrial action potential after prolonged atrial fibrillation. The dotted line indicates a normal atrial action potential morphology.

The present example demonstrates therapeutic lengthening of the action potential The cellular adaptive processes that occur with AF are completely different than those seen with heart failure. During sustained AF, there is a shortening of the APD and refractory period, essentially with loss of the plateau phase of the action potential (FIG. 6). Clinical and experimental studies have shown a 70% downregulation of the $Ca^{2+}$ current, $I_{CaL}$, and the transient outward current, $I_{to}$, to account for the observed changes in the AP morphology. The inward rectifier and adenosine/acetylcholine activated potassium currents ($I_{K1}$ and $I_{K,Ach}$) are upregulated. The end result of these changes is an improved ability of the atrial myocytes to sustain the rapid and chaotic impulses characteristic of atrial fibrillation. This situation creates a cycle where the rapid rate causes a shortened refractory period which allows the continuation of the rapid rate, an idea that has been termed "AF begets AF". The maladaptive nature of the ion channel alterations suggests that interrupting these changes on a molecular level is a potential treatment for AF.

FIG. 6 specifically shows changes in the atrial action potential after prolonged atrial fibrillation. Reduction in the transient outward current, Ito, and the 1-type calcium current, ICa,1 result in a decreased notch and plateau. A normal action potential is noted by the dashed line.

To evaluate the ability of potassium channel gene transfer to extend the plateau phase of the action potential, the guinea pig model illustrated in example 5 was used.[3] Rather than injecting AdHERG to shorten the action potential, AdHERG-G628S was injected. This mutant reduced the intrinsic HERG and extended the plateau of the action potential in a controllable fashion. $I_{Kr}$ current density was reduced by 80%, which caused a 17% increase in APD (FIGS. 7A–B).[3] Observation of the action potential morphology shows that the increase in APD occurs by extension of the plateau phase of the action potential. When applied to atrial fibrillation, this extension of the action potential would have an effect similar to that of potassium channel blocking drugs and reduce the occurrence of atrial fibrillation. Since the gene transfer-mediated increase would be specific to the atria, it would eliminate the ventricular proarrhythmic effects caused by antiarrhythmic drugs.

Figure 7B:
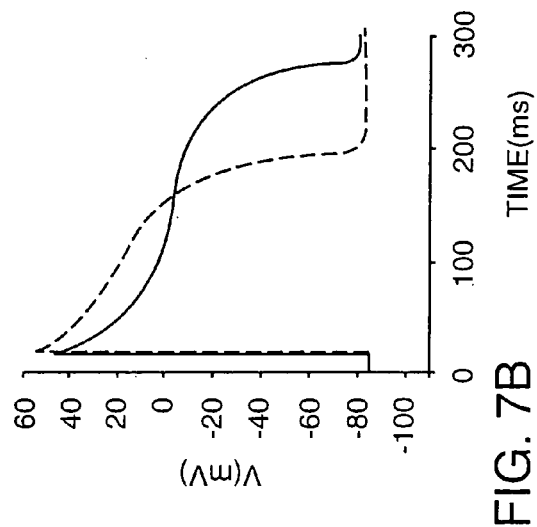
FIG. 7B is a photograph showing related action potential (AP) of the mutant HERG.
Figure 7A:
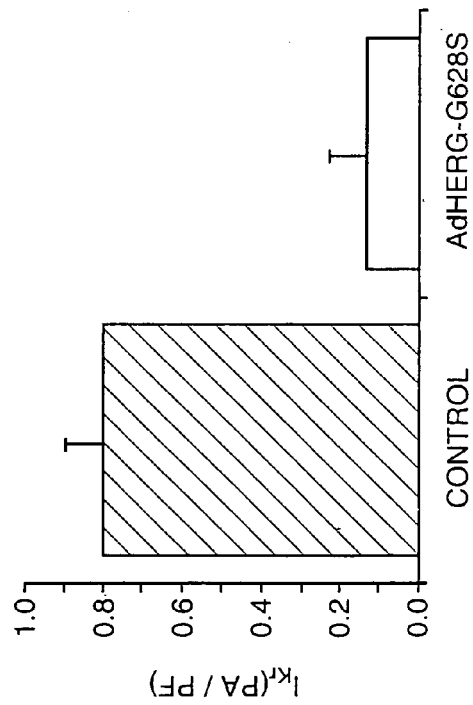
FIG. 7A is a graph showing comparison of $I_{kr}$ current in presence and absence of gene transfer-mediated overexpression of dominant-negative mutant of HERG.

FIGS. 7A–B are explained in more detail as follows. FIG. 7A shows comparison of $I_{Kr}$ current in the presence or absence of gene transfer-mediated overexpression of a dominant negative mutant of HERG. FIG. 7B. Photograph of an action potential tracing from a cell overexpressing the mutant HERG.

EXAMPLE 7

Construction and Use of a Biopacemaker

Patients who suffer heart block or other cardiac conduction system disorders require placement of an electronic pacemaker to maintain adequate blood flow. While this treatment is standard practice (about 250,000 cardiac pacemakers are implanted annually in the U.S.), it is expensive ($45,000 10-year cost) and carries substantial risk (infection, pneumothorax, etc.). A potential application of the invention is to increase automaticity of focal regions in the sinus node, atria, atrioventricular node, His-Purkinje system or ventricles in order to replicate the activity of the native pacemaker.

In proof of principle experiments, guinea pigs underwent surgical injection of AdcgiKir2.1AAA. After sufficient time for protein expression had elapsed, the cardiac myocytes were isolated and analyzed using conventional electrophysiological techniques. Adult guinea pigs (200–250 g) received metafane anesthesia. A left lateral thoracotomy was performed in sterile surgical fashion. The aorta was isolated. A cannula was passed through the LV apex into the proximal aorta. The aorta was cross-clamped and 0.15 ml of Kreb's solution containing AdKir2.1AAA was injected over 40 seconds. The cross clamp and cannula were removed; the incisions were closed, and the animal was allowed to recover. After 3 days, the animal was sacrificed. The heart was removed and cardiac myocytes were enzymatically isolated using conventional methods. Cells infected with the virus were identified by the presence of GFP fluorescence. No uninfected cells exhibited automaticity, while several AdcgiKir2.1AAA infected cells displayed spontaneous, regularly occurring action potentials. Examples of uninfected and infected cells are displayed in FIGS. 10A–B.

Figure 10B:
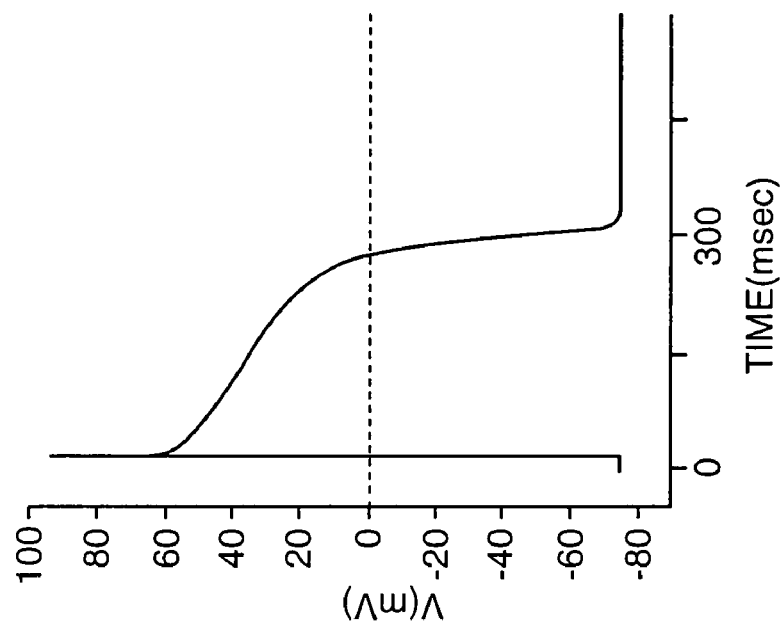
FIGS. 10A–B are graphs showing action potentials in guinea pig ventricular myocytes expressing Kir2.1AAA.
Figure 10A:
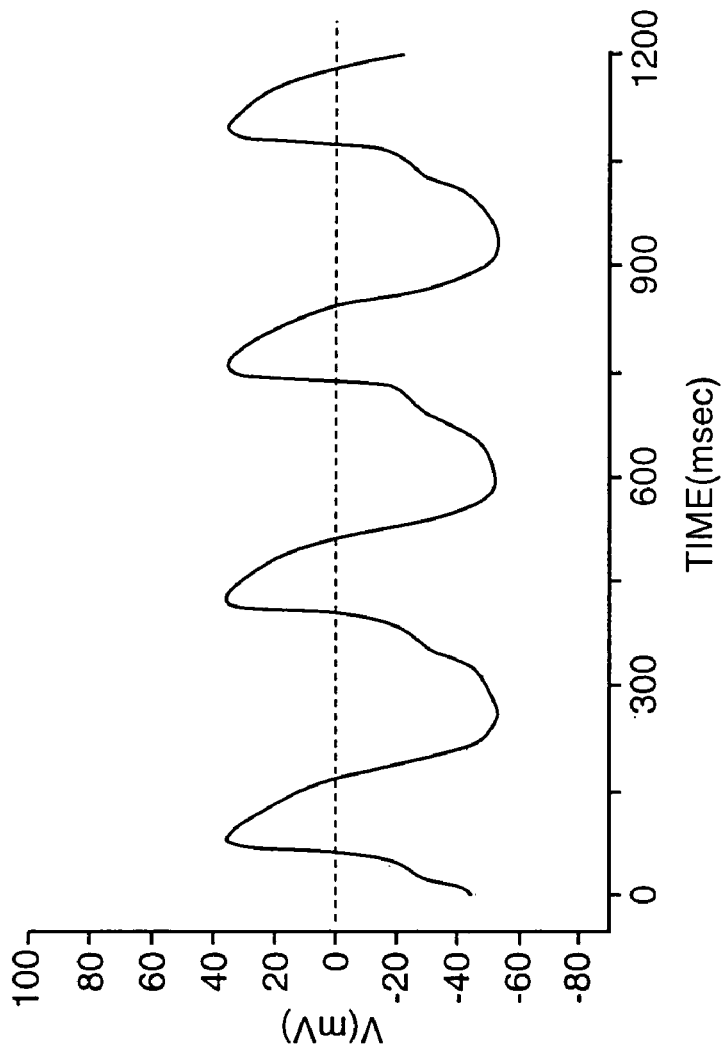

FIGS. 10A–B are explained in more detail as follows. FIG. 10A. Spontaneously occurring action potentials in guinea pig ventricular myocytes expression Kir2.1AAA. FIG. 10B Induced action potential from a control myocyte. No spontaneous action potentials were observed in control cells.

The following materials and methods were used as needed in the foregoing Examples.

Adenoviruses-I. Adβgal was a gift; the vector contained the E. coli lac Z gene driven by the human cytomegalovirus (CMV) immediate early promoter. $AdG_i$ was constructed using a previously reported method[19]. The vector included the full-length rat $G\alpha_{i2}$ gene driven by the CMV promoter. Virus stock expansion and quality control were performed as previously described[4].

Gene Transfer Procedure. Immediately prior to catheterization, female domestic swine (30–40 kg) received sustained release diltiazem 180 mg, aspirin 325 mg and sildenafil 25 mg orally, and a mixture of ketamine 100 mg and acepromazine 4 mg intramuscularly. (For uniformity, the same pretreatment regimen, except administration of sildenafil, was used for all procedures to control for any effect these agents might have on the baseline EP measurements.) After sedation, anesthesia was induced with 5–10 ml of intravenous sodium pentothal 2.5% solution and maintained with inhaled isoflurane 2% in oxygen. The right carotid artery, right internal jugular vein and right femoral vein were accessed by sterile surgical technique, and introducer sheaths were inserted into each vessel. After baseline EP study (as described below), the right coronary artery was catheterized via the right carotid artery, using a 7 Fr. angioplasty guiding catheter. The AV nodal branch was selected with a 0.014" guide wire, over which a 2.7 Fr. infusion catheter was inserted into the AV nodal artery. The following solutions were infused through the catheter: 10 ml of normal saline (S) containing 5 μg of $VEGF_{165}$ and 200 μg of nitroglycerin over 3 minutes, 1 ml of normal saline containing $7.5\times10^9$ pfu of adenovirus and 20 μg of nitroglycerin over 30 seconds, and 2 ml of normal saline over 30 seconds. After recovery from anesthesia, the animals received usual care and no additional medication. After one week, repeat EP evaluation was performed; the animals were sacrificed, and the organs were removed for histological evaluation.

Electrophysiological Evaluation. Immediately prior to gene transfer and one week afterward, the animals underwent electrophysiological evaluation. A 5 Fr. steerable quadripolar EP catheter was placed through the right internal jugular vein into the high right atrium; a 5 Fr. non-steerable quadripolar EP catheter was placed through the same internal jugular vein into the right ventricle, and a 6 Fr. non-steerable quadripolar EP catheter was placed through the right femoral vein into the His bundle position. Baseline intracardiac electrograms were obtained, and electrocardiographic intervals were recorded. Following standard techniques, the AVNERP was measured by programmed stimulation of the right atrium with a drive train cycle length of 400 msec.

After baseline measurements were obtained, atrial fibrillation was induced by burst atrial pacing from a cycle length of 180 msec decrementing to 100 msec over 30 sec. Three attempts were made using this induction protocol. If no sustained atrial fibrillation was induced, the atria were paced at an output of 10 mA and a cycle length of 20 msec for 15 sec. The latter protocol reliably induced atrial fibrillation. The first episode of atrial fibrillation lasting longer than 12 sec was used for analysis. The median duration for atrial fibrillation episodes was 20 sec (range 14–120 sec). The heart rate was determined by measuring R—R intervals during the first 10 seconds of atrial fibrillation (average number of R—R intervals measured was 32 per recording). After conversion back to sinus rhythm, 1 mg of epinephrine was administered through the femoral venous sheath. Atrial fibrillation was re-induced in the presence of epinephrine (median episode duration 131 sec, range 20 sec-10 min), and the heart rate was again measured (average number of R—R intervals measured was 60 per recording). In the drug-free state, all episodes of atrial fibrillation terminated spontaneously. After epinephrine infusion, 4 episodes persisted for 10 minutes and were terminated by electrical cardioversion.

Histological Evaluation. After euthanasia, the heart and sections of lung, liver, kidney, skeletal muscle and ovary were removed and rinsed thoroughly in PBS. The atrial and ventricular septa were dissected from the heart and frozen to −80° C. The remaining portions of the heart and other organs were sectioned, and alternating sections were used for gross or microscopic analysis. The sections for gross examination were fixed in 2% formaldehyde/0.2% glutaraldehyde for 15 minutes at room temperature, and stained for 6 hours at 37° C. in PBS containing 1.0 mg/ml 5-bromo, 4-chloro, 3-indolyl-β-D-galactopy (X-gal), 15 mmol/L potassium ferricyanide, 15 mmol/L potassium ferrocyanide and 1 mmol/L $MgCl_2$. After staining, the slices were fixed with 2% formaldehyde/0.2% glutaraldehyde in PBS at 4° C. overnight. The sections for microscopic analysis were embedded in paraffin, cut to 7 μm thickness, stained with X-gal solution as above and counterstained with Hematoxylin and eosin stains using traditional methods. β-galactosidase expression in the AV node was quantified by counting 100 cells in randomly chosen high-power fields of microscopic sections through the region.

Western Blot Analysis of $G\alpha_{i2}$ Expression. To quantify $G\alpha_{i2}$ gene expression, Western blot analysis of $G\alpha_{i2}$ protein expression was performed on cytosolic extracts of frozen AV nodal tissue (Novex System). Samples were normalized for protein content, and SDS-polyacrylamide gel electrophoresis of the normalized samples was performed on 4–12% gradient gels. Proteins were then transferred to nitrocellulose membranes (30V, 1 hr). Detection of protein was performed by sequential exposure to Western Blocking Reagent (Boehringer Mannheim), a mouse monoclonal antibody against $G\alpha_{i2}$ (Neomarkers, 1 ug/ml, 2 hours), and goat-anti-mouse secondary antibody conjugated with horseradish peroxidase (NEN, 1:10000, 30 min). Bands were detected with the enhanced chemiluminescence assay (Amersham) and quantified using the Quantity One software package (BioRad).

Statistical Analysis. The data are presented as mean±s.e.m. Statistical significance was determined at the 5% level using the student's t test and repeated measures ANOVA, where appropriate.

The following materials and methods were specifically employed in Examples 4–6, above.

Adenovirus vectors-II. Adβgal, AdGi, AdHERG, and AdHERG-G628S are recombinant adenoviruses encoding β-galactosidase, wild-type $G\alpha_{i2}$, wild-type HERG, and HERG-G628S—a mutant of HERG found in some long QT syndrome patients. $G\alpha_{i2}$ is the second isoform of the alpha-subunit of the inhibitory G protein, and HERG is a potassium channel. Expression of the mutant channels reduces the intrinsic current of the respective channel, and overexpression of the wild-type channel increases the intrinsic current. AdegiKir2.1AAA is a bicistronic adenoviral construct with enhanced GFP and Kir2.1 AAA genes connected by an IRES sequence. By use of the IRES sequence, a single ecdysone promoter is capable of driving expression of both genes. The Kir2.1AAA mutant replaces GYG in the pore region with AAA, causing dominant negative suppression of Kir2.1.

All of the adenoviruses were created using standard methods. For Adβgal and AdGi, the CMV immediate-early promoter was used to drive gene expression, and for AdHERG, AdHERG-G628S and AdegiKir2.1AAA expression was driven by the ecdysone promoter system. Any promoter capable of driving expression of the transgene would be suitable under most circumstances. Virus stocks were maintained in phosphate buffered saline with 10% glycerol and 1 mM $MgCl_2$. Virus quality control included wild-type virus assay, infectious titre measurement by plaque assay, and transgene expression measurement by Western blot and functional assay appropriate to the specific gene.

See also the PCT application PCT/US98/23877 to Marban E. for additional disclosure relating to polynucleotides used in accord with the present invention.

The following references (referred to by number througout the text with the exception of Examples 4–6) are specifically incorporated herein by reference.

1. MacMahon, S., Collins, R., Peto, R., Koster, R. & Yusuf, S. Effect of prophylactic lidocaine in suspected acute myocardial infarction: an overview of results from the randomized, controlled trials. *JAMA* 260, 1910–1916 (1988).
2. Echt, D. et al. Mortality and morbidity in patients receiving encainide, flecainide, or placebo. *N Engl J Med* 324, 781–788 (1991).
3. Waldo, A. et al. Effect of d-sotalol on mortality in patients with left ventricular dysfunction after recent and remote myocardial infarction. *Lancet* 348, 7–12 (1996).
4. Donahue, J. K., Kikkawa, K., Johns, D., Marban, E. & Lawrence, J. Ultrarapid, highly efficient viral gene transfer to the heart. *Proc Natl Acad Sci USA* 94, 4664–4668 (1997).
5. Donahue, J. K., Kikkawa, K., Thomas, A. D., Marban, E. & Lawrence, J. Acceleration of widespread adenoviral gene transfer to intact rabbit hearts by coronary perfusion with low calcium and serotonin. *Gene Therapy* 5, 630–634 (1998).
6. Wu, H. M., Huang, Q., Yuan, Y. & Granger, H. J. VEGF induces NO-dependent hyperpermeability in coronary venules. *Am J Physiol* 271, H2735–H2739 (1996).
7. Muhlhauser, J. et al. Safety and efficacy of in vivo gene transfer into the porcine heart with replication-deficient, recombinant adenovirus vectors. *Gene Therapy* 3, 145–153 (1996).
8. French, B., Mazur, W., Geske, R. & Bolli, R. Direct in vivo gene transfer into porcine myocardium using replication-deficient adenoviral vectors. *Circulation* 90, 2414–2424 (1994).
9. Kass-Eisler, A. et al. Quantitative determination of adenovirus-mediated gene delivery to rat cardiac myocytes in vitro and in vivo. *Proc Natl Acad Sci USA* 90, 11498–11502 (1993).
10. Kass-Eisler, A. et al. The Impact of Developmental Stage, Route of Administration and the Immune System on Adenovirus-Mediated Gene Transfer. *Gene Therapy* 1, 395–402 (1994).
11. Eschenhagen, T. G proteins and the heart. *Cell Biol Int* 17, 723–749 (1993).
12. Dessauer, C., Posner, B. & Gilman, A. Visualizing signal transduction: receptors, G-proteins, and adenylate cyclases. *Clin Sci (Colch)* 91, 527–537 (1996).
13. Quinones, M. et al. Avoidance of immune response prolongs expression of genes delivered to the adult rat myocardium by replication defective adenovirus. *Circulation* 94, 1394–1401 (1996).
14. Channon, K. et al. Acute host-mediated endothelial injury after adenoviral gene transfer in normal rabbit arteries: impact on transgene expression and endothelial function. *Circ Res* 82, 1253–1262(1998).
15. Lafont, A. et al. Thrombus generation after adenovirus-mediated gene transfer into atherosclerotic arteries. *Hum Gene Ther* 9, 2795–2800 (1998).
16. Cichon, G. et al. Intravenous administration of recombinant adenoviruses causes thrombocytopenia, anemia, and erythroblastosis in rabbits. *J Gene Med* 1, 360–371 (1999).
17. Marshall, E. Gene therapy death prompts review of adenovirus vector. *Science* 286, 2244–2245 (1999).
18. Pauschinger, M. et al. Detection of adenoviral genome in the myocardium of adult patients with idiopathic left ventricular dysfunction. *Circulation* 99, 1348–1354 (1999).
19. Akhter, S. et al. Restoration of beta-adrenergic signaling in failing cardiac ventricular myocytes via adenoviral-mediated gene transfer. *Proc Natl Acad Sci USA* 94, 12100–12105 (1997).

The following references are also incorporated by reference. Each reference is referred to by number only in Examples 4–6, above.

1. Khand A, Rankin A, Kaye G, Cleland J. Systematic review of the management of atrial fibrillation in patients with heart failure. *Eur Heart J* 2000;21:614–632.
2. Donahue J K, Heldman A H, Fraser H, McDonald A D, Miller J M, Rade J J, Eschenhagen T, Marbán E. Focal Modification of Electrical Conduction in the Heart by Viral Gene Transfer. *Nature Med* 2000;6:1395–1398.

3. Hoppe U C, Marbán E, Johns D C. Distinct gene-specific mechanisms of arrhythmia revealed by cardiac gene transfer of two long QT disease genes, HerG and KCNE1. *Proc Nat Acad Sci* 2001;98:5335–5340.

All references are incorporated herein by reference.

The invention has been described in detail with reference to preferred embodiments thereof. However, it will be appreciated that those skilled in the art, upon consideration of the disclosure, may make modification and improvements within the spirit and scope of the invention.

---

What is claimed is:

1. A unitary catheter drug delivery device having a proximal end and a distal end, said device comprising in combination:
   an apparatus for delivery of a polynucleotide to a patient;
   a reservoir housing a polynucleotide encoding a human protein selected from the group consisting of: a wild-type inhibitory $G\alpha_{i2}$ protein subunit, and a constitutively active $G\alpha_{i2}$ subunit;
   an apparatus for detection of position of the device within the patient: and
   electrodes for detecting position of the distal end.

2. The device of claim 1 wherein the device is adapted for an endoscopic procedure.

3. The unitary catheter drug delivery device of claim 1, wherein the device further comprises an injector connection or tubing spaced between the proximal and distal ends of the device.

4. The unitary catheter drug delivery device of claim 3, wherein the device further comprises electrode cables within the injector connection or tubing, the electrode cables communicating with the electrodes and an electrical connection positioned at the proximal end of the device.

5. The unitary catheter drug delivery device of claim 4, wherein the electrical connection is adapted to activate the electrodes, the electrodes being positioned at the distal end of the device.

6. The unitary catheter drug delivery device of claim 1, wherein the device further comprises a needle extension mechanism at the distal end of the device.

7. The unitary catheter drug delivery device of claim 1, wherein the device further comprises a steering control near the proximal end of the device.

8. The unitary catheter drug delivery device of claim 1, wherein the electrodes are positioned around the distal end of the device.

9. The unitary catheter drug delivery device of claim 1, wherein the a polynucleotide encodes constitutively active $G\alpha_{i2}$.

10. The unitary catheter drug delivery device of claim 1 wherein the polynucleotide encodes wild-type $G\alpha_{i2}$.

11. The unitary catheter drug delivery device of claim 1 wherein the polynucleotide encodes wild-type $G\alpha_{i2}$ as shown in SEQ ID NO: 2.

12. A unitary catheter drug delivery device having a proximal end and a distal end, said device comprising in combination:
   an apparatus for delivery of a polynucleotide to a patient;
   an apparatus for detection of position of the device within the patient; electrodes
   for detecting position of the distal end;
   an injector connection or tubing spaced between the proximal and distal ends of the device;
   electrode cables within the injector connection or tubing for communicating with the electrodes;
   an electrical connection positioned at the proximal end of the device;
   a reservoir housing a polynucleotide encoding a human protein selected from the group consisting of: wild-type inhibitory $G\alpha_{i2}$ protein subunit and a constitutively active $G\alpha_{i2}$ subunit; and
   a needle extension mechanism at the distal end, wherein the electrodes are positioned at the distal end of the device and are spaced from each other by the injector connection or tubing.

13. The unitary catheter drug delivery device of claim 12 wherein the polynucleotide encodes constitutively active $G\alpha_{i2}$.

14. The unitary catheter drug delivery device of claim 12 wherein the polynucleotide encodes wild-type $G\alpha_{i2}$.

15. The unitary catheter drug delivery device of claim 12 wherein the polynucleotide encodes wild-type $G\alpha_{i2}$ as shown in SEQ ID NO: 2.

* * * * *

SEQUENCE LISTING

<160> NUMBER OF SEQ ID NOS: 10

<210> SEQ ID NO 1
<211> LENGTH: 843
<212> TYPE: DNA
<213> ORGANISM: Homo sapiens

<400> SEQUENCE: 1

```
cccggccttt ttttttcctt tttcgactag ctgcaaccca gagggagaag gcggtaaacc      60
cgccttaaga ctgagaaaac cgcagtccag aaaggctccc gagttcgtag atcccaaaac     120
aagtttactg gactcattaa ctttaacaaa tgacaaagac acgcctcctc cacctaactc     180
gcccaactcg cagaagctca gagggctggt tcctgctctg ccctcgaggg caccgatccc     240
caccctcggg ttaacagatc cgccctcccg gctgtccagc aacagagctc ccggcgcttc     300
gcacccaatc acagcccggt cccgcctgca gcccgcccag tgccgggtcc cggggttttgg    360
aaccacccct attgccttt ctccgcgtgg ccccgcctgc acccaggccc gagcctgggc      420
tgcctaactt ccccttcgc tccgcccctcg agccaatcaa cagcctctaa tctcctctgg     480
ccccgcctgc aagcccgccc cggcccagtc acaggcttgg ttcgcccagg ccccaccccc     540
ggcccgcccc gccgtcggtg cgcggcggta gggaaggcgc ctcccgcagt cgctcggaac     600
tgccgacccg agtgcttccc gcagagggct ggtggtggga gcggagtggg tcgggcgggg    660
ccgagccggg ccgtgggccg tgtggggcc gggcggcggc cggcggcg gacgcggga     720
tgggctgcac cgtgagcgcc gaggacaagg cggcggccga gcgctctaag atgatcgaca     780
agaacctgcg ggaggacgga gagaaggcgg cgcgggaggt gaagttgctg ctgttgggtg     840
agg                                                                    843
```

<210> SEQ ID NO 2
<211> LENGTH: 63
<212> TYPE: DNA
<213> ORGANISM: Homo sapiens

<400> SEQUENCE: 2

```
gccctctgtt ccaggtgctg gggagtcagg gaagagcacc atcgtcaagc agatgaagta      60
agt                                                                     63
```

<210> SEQ ID NO 3
<211> LENGTH: 162
<212> TYPE: DNA
<213> ORGANISM: Homo sapiens

<400> SEQUENCE: 3

```
gtcctggcta tcaggatcat ccacgaggat ggctactccg aggaggaatg ccggcagtac      60
cgggcggttg tctacagcaa caccatccag tccatcatgg ccattgtcaa agccatgggc     120
aacctgcaga tcgactttgc cgaccccctcc agagcggtat gt                        162
```

<210> SEQ ID NO 4
<211> LENGTH: 181
<212> TYPE: DNA

```
<213> ORGANISM: Homo sapiens

<400> SEQUENCE: 4
gccactgtgc ccaggacgac gccaggcagc tatttgcact gtcctgcacc gccgaggagc      60
aaggcgtgct ccctgatgac ctgtccggcg tcatccggag gctctgggct gaccatggtg     120
tgcaggcctg ctttggccgc tcaagggaat accagctcaa cgactcagct gcctagtgag     180
t                                                                     181

<210> SEQ ID NO 5
<211> LENGTH: 149
<212> TYPE: DNA
<213> ORGANISM: Homo sapiens

<400> SEQUENCE: 5 cccccccatcc ccagctacct gaacgacctg gagcgtattg cacagagtga ctacatcccc     60
acacagcaag atgtgctacg gacccgcgta aagaccacgg ggatcgtgga gacacacttc    120
accttcaagg acctacactt caagtgagc                                       149

<210> SEQ ID NO 6
<211> LENGTH: 142
<212> TYPE: DNA
<213> ORGANISM: Homo sapiens

<400> SEQUENCE: 6
ctgcaggatg tttgatgtgg gtggtcagcg gtctgagcgg aagaagtgga tccactgctt      60
tgagggcgtc acagccatca tcttctgcgt agccttgagc gcctatgact tggtgctagc    120
tgaggacgag gagatggtga ga                                              142

<210> SEQ ID NO 7
<211> LENGTH: 174
<212> TYPE: DNA
<213> ORGANISM: Homo sapiens

<400> SEQUENCE: 7
tattctaccc ccagaaccgc atgcatgaga gcatgaagct attcgatagc atctgcaaca      60
acaagtggtt cacagacacg tccatcatcc tcttcctcaa caagaaggac ctgtttgagg    120
agaagatcac acacagtccc ctgaccatct gcttccctga gtacacaggt gtgg           174

<210> SEQ ID NO 8
<211> LENGTH: 235
<212> TYPE: DNA
<213> ORGANISM: Homo sapiens

<400> SEQUENCE: 8
tttctctccc ccaggggcca acaaatatga tgaggcagcc agctacatcc agagtaagtt      60
tgaggacctg aataagcgca aagacaccaa ggagatctac acgcacttca cgtgcgccac    120
cgacaccaag aacgtgcagt tcgtgtttga cgccgtcacc gatgtcatca tcaagaacaa    180
cctgaaggac tgcggcctct tctgaggggc agcggggcct ggcgggatgg tgatc          235

<210> SEQ ID NO 9
<211> LENGTH: 1036
<212> TYPE: DNA
<213> ORGANISM: Homo sapiens

<400> SEQUENCE: 9 gctttcccccc acctccaggg ccaccgccga ctttgtaccc cccaacccct gaggaagatg      60
```

```
ggggcaagaa gatcacgctc cccgcctgtt ccccgccgc ttttctcctc tttcctctct      120
ttgttctcag ctcccctgt ccctcagct ccagacgtag gggaggggtt gccacaggcc       180
tccctgtttg aagcctgccc ttgtctgaga tgctggtaat ggccatggta ccccttctg      240 ggcatctgtt ctggtttta accattgtct tgttctgtga tgaggggagg ggggcacatg     300
ctgagtctcc caaggctgcg tctggagggg cccctgcttc tccagcctgg acccccagct    360
ttgcccaaca ccagcccctg ccccagccca agtccaaatg tttacaggga gcctcctgcc    420
cagtccccca accccagccg ctcggaggcc caaaggaaaa agcacaaga agcgtgagac     480 gccaccattc ctggaaacca cagtccacct gctcattctc gtagctttt aaaaaaatga     540 aagtaaagga aaaaaaaaa actgaaatct agaaaacttt ttagagaaaa actatttaaa    600
actgtcagat cctgaccagc aagccccccc ccagccccc ttccaagtga ctccgtgcct    660
tgagtgtgtc tgcgtgttta caccgtccc tctgctggcc gccccgtgc gagcggcacc     720 cctgccctgc cctccacaga attgggttcc aagggctgtt ccagacaact gccaacgtca   780
ctgagggccc tgccccagcg gccctggccc caggctctat taacctaaaa tgtagctccc   840
tagcgctaac ctaggaaccg ccgctgcctg ctgggggcc acgcccctca tgcccttgtc    900
ccaggcccgg ggccttcagc gttgaacact tccttgcttt tttcacatgt tttatggaat   960
tgttcacctg gtttgaaata ataaaatgta gaaagaaaaa aaataccgag aactgatggg  1020
tattctctcc cagggg                                                    1036

<210> SEQ ID NO 10
<211> LENGTH: 355
<212> TYPE: PRT
<213> ORGANISM: Homo sapiens

<400> SEQUENCE: 10

Met Gly Cys Thr Val Ser Ala Glu Asp Lys Ala Ala Glu Arg Ser
 1               5                  10                  15

Lys Met Ile Asp Lys Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
        35                  40                  45

Ile Val Lys Gln Met Lys Ile Ile His Glu Asp Gly Tyr Ser Glu Glu
    50                  55                  60

Glu Cys Arg Gln Tyr Arg Ala Val Val Tyr Ser Asn Thr Ile Gln Ser
65                  70                  75                  80

Ile Met Ala Ile Val Lys Ala Met Gly Asn Leu Gln Ile Asp Phe Ala
                85                  90                  95

Asp Pro Ser Arg Ala Asp Asp Ala Arg Gln Leu Phe Ala Leu Ser Cys
            100                 105                 110

Thr Ala Glu Glu Gln Gly Val Leu Pro Asp Asp Leu Ser Gly Val Ile
        115                 120                 125

Arg Arg Leu Trp Ala Asp His Gly Val Gln Ala Cys Phe Gly Arg Ser
    130                 135                 140

Arg Glu Tyr Gln Leu Asn Asp Ser Ala Ala Tyr Tyr Leu Asn Asp Leu
145                 150                 155                 160

Glu Arg Ile Ala Gln Ser Asp Tyr Ile Pro Thr Gln Gln Asp Val Leu
                165                 170                 175

Arg Thr Arg Val Lys Thr Thr Gly Ile Val Glu Thr His Phe Thr Phe
            180                 185                 190
```

-continued

```
Lys Asp Leu His Phe Lys Met Phe Asp Val Gly Gly Gln Arg Ser Glu
        195                 200                 205
Arg Lys Lys Trp Ile His Cys Phe Glu Gly Val Thr Ala Ile Ile Phe
        210                 215                 220
Cys Val Ala Leu Ser Ala Tyr Asp Leu Val Leu Ala Glu Asp Glu Glu
225                 230                 235                 240
Met Asn Arg Met His Glu Ser Met Lys Leu Phe Asp Ser Ile Cys Asn
                245                 250                 255
Asn Lys Trp Phe Thr Asp Thr Ser Ile Ile Leu Phe Leu Asn Lys Lys
            260                 265                 270
Asp Leu Phe Glu Glu Lys Ile Thr His Ser Pro Leu Thr Ile Cys Phe
        275                 280                 285
Pro Glu Tyr Thr Gly Ala Asn Lys Tyr Asp Glu Ala Ala Ser Tyr Ile
        290                 295                 300
Gln Ser Lys Phe Glu Asp Leu Asn Lys Arg Lys Asp Thr Lys Glu Ile
305                 310                 315                 320
Tyr Thr His Phe Thr Cys Ala Thr Asp Thr Lys Asn Val Gln Phe Val
                325                 330                 335
Phe Asp Ala Val Thr Asp Val Ile Ile Lys Asn Asn Leu Lys Asp Cys
            340                 345                 350
Gly Leu Phe
        355
```